(12) United States Patent
Andersen et al.

(10) Patent No.: US 9,096,837 B2
(45) Date of Patent: Aug. 4, 2015

(54) ALPHA-AMYLASE VARIANTS WITH ALTERED PROPERTIES

(75) Inventors: Carsten Andersen, Vaerlose (DK); Henrik Ostdal, Virum (DK); Peter Skagerlind, Hoganas (SE)

(73) Assignee: Novozymes A/S, Bagsvaerd (DK)

(*) Notice: Subject to any disclaimer, the term of this patent is extended or adjusted under 35 U.S.C. 154(b) by 1146 days.

(21) Appl. No.: 13/008,619

(22) Filed: Jan. 18, 2011

(65) Prior Publication Data

US 2011/0136205 A1 Jun. 9, 2011

Related U.S. Application Data

(63) Continuation of application No. 11/571,708, filed as application No. PCT/DK2005/000469 on Jul. 5, 2005, now abandoned.

(60) Provisional application No. 60/609,065, filed on Sep. 10, 2004, provisional application No. 60/585,763, filed on Jul. 6, 2004.

(30) Foreign Application Priority Data

Jul. 5, 2004 (DK) .............................. 2004 01059
Sep. 2, 2004 (DK) .............................. 2004 01325

(51) Int. Cl.
C12N 9/26 (2006.01)
C12P 21/06 (2006.01)
C07H 21/02 (2006.01)
C07K 1/00 (2006.01)
C12N 9/28 (2006.01)

(52) U.S. Cl.
CPC .......... *C12N 9/2417* (2013.01); *C07K 2299/00* (2013.01)

(58) Field of Classification Search
CPC .................... C12N 9/2417; C07K 2299/00
USPC ................... 435/201; 536/23.1, 23.2; 530/350
See application file for complete search history.

(56) References Cited

U.S. PATENT DOCUMENTS

| | | | |
|---|---|---|---|
| 6,093,562 A | 7/2000 | Bisgard-Frantzen et al. | |
| 6,528,298 B1 | 3/2003 | Svendsen et al. | |
| 7,432,099 B2 * | 10/2008 | Andersen et al. | 435/201 |
| 8,609,811 B2 * | 12/2013 | Andersen et al. | 530/350 |
| 2003/0129718 A1 | 7/2003 | Andersen et al. | |
| 2003/0171236 A1 | 9/2003 | Svendsen et al. | |
| 2004/0096952 A1 | 5/2004 | Svendsen et al. | |

FOREIGN PATENT DOCUMENTS

| WO | WO 96/23873 A1 | 8/1996 |
|---|---|---|
| WO | WO 99/23211 A1 | 5/1999 |
| WO | 0022103 A1 | 4/2000 |
| WO | WO 00/60060 A2 | 10/2000 |
| WO | WO 01/66712 A2 | 9/2001 |
| WO | 0188107 A2 | 11/2001 |
| WO | 0196537 A2 | 12/2001 |
| WO | 0210355 A2 | 2/2002 |
| WO | 02092797 A2 | 11/2002 |

* cited by examiner

*Primary Examiner* — Ganapathirama Raghu
(74) *Attorney, Agent, or Firm* — Michael W. Krenicky

(57) ABSTRACT

The present disclosure relates to variants (mutants) of polypeptides, in particular Termamyl-like alpha-amylases, which variant has alpha-amylase activity and exhibits an alteration in at least one of the following properties relative to said parent alpha-amylase: substrate specificity, substrate binding, substrate cleavage pattern, thermal stability, pH/activity profile, pH/stability profile, stability towards oxidation, Ca2+ dependency, specific activity, in particular laundry and dish-wash applications.

21 Claims, 4 Drawing Sheets

```
                      1                                                50
         BLA    (1)  --ANLNGTLMQYFEWYMPNDGQHWKRLQNDSAYLAEHGITAVWIPPAYKG
     AMY1048    (1)  -SVPVNGTMMQYFEWYLPDDGTLWTKVANNAQSLANLGITALWLPPAYKG
         BSG    (1)  -AAPFNGTMMQYFEWYLPDDGTLWTKVANEANNLSSLGITALWLPPAYKG
         BAN    (1)  ---AVNGTLMQYFEWYTPNDGQHWKRLQNDAEHLSDIGITAVWIPPAYKG
    B.sp.K38    (1)  --DGLNGTMMQYYEWHLENDGQHWNRLHDDAAALSDAGITAIWIPPAYKG
       AAI-10   (1)  HHDGTNGTIMQYFEWNVPNDGQHWNRLHNNAQNLKNAGITAIWIPPAWKG
       SP722    (1)  HHNGTNGTMMQYFEWHLPNDGNHWNRLRDDASNLRNRGITAIWIPPAWKG
       SP690    (1)  HHNGTNGTMMQYFEWYLPNDGNHWNRLRDDAANLKSKGITAVWIPPAWKG
       AA560    (1)  HHNGTNGTMMQYFEWYLPNDGNHWNRLRSDASNLKDKGISAVWIPPAWKG
     Amrk385    (1)  HHNGTNGTMMQYFEWHLPNDGQHWNRLRNDAANLKNLGITAVWIPPAWKG
    B.sp.707    (1)  HHNGTNGTMMQYFEWYLPNDGNHWNRLNSDASNLKSKGITAVWIPPAWKG
    B.sp.7-7    (1)  HHNGTNGTMMQYFEWYLPNDGNHWNRLRSDASNLKDKGITAVWIPPAWKG
  KSM-AP1378    (1)  HHNGTNGTMMQYFEWHLPNDGNHWNRLRDDAANLKSKGITAVWIPPAWKG 51                                              100
         BLA   (49)  TSQADVGYGAYDLYDLGEFHQKGTVRTKYGTKGELQSAIKSLHSRDINVY
     AMY1048   (50)  TSSSDVGYGVYDLYDLGEFNQKGTVRTKYGTKTQYIQAIQAAHTAGMQVY
         BSG   (50)  TSRSDVGYGVYDLYDLGEFNQKGTVRTKYGTKAQYLQAIQAAHAAGMQVY
         BAN   (48)  LSQSDNGYGPYDLYDLGEFQQKGTVRTKYGTKSELQDAIGSLHSRNVQVY
    B.sp.K38   (49)  NSQADVGYGAYDLYDLGEFNQKGTVRTKYGTKAQLERAIGSLKSNDINVY
       AAI-10  (51)  TSQNDVGYGAYDLYDLGEFNQKGTVRTKYGTKAELERAIRSLKANGIQVY
       SP722   (51)  TSQNDVGYGAYDLYDLGEFNQKGTVRTKYGTRSQLESAIHALKNNGVQVY
       SP690   (51)  TSQNDVGYGAYDLYDLGEFNQKGTVRTKYGTRNQLQAAVTSLKNNGIQVY
       AA560   (51)  ASQNDVGYGAYDLYDLGEFNQKGTIRTKYGTRNQLQAAVNALKSNGIQVY
     Amrk385   (51)  TSQNDVGYGAYDLYDLGEFNQKGTIRTKYGTRSQLQSAIASLQNNGIQVY
    B.sp.707   (51)  ASQNDVGYGAYDLYDLGEFNQKGTVRTKYGTRSQLQAAVTSLKNNGIQVY
    B.sp.7-7   (51)  ASQNDVGYGAYDLYDLGEFNQKGTVRTKYGTRNQLQAAVTALKNNGIQVY
  KSM-AP1378   (51)  TSQNDVGYGAYDLYDLGEFNQKGTVRTKYGTRSQLQGAVTSLKNNGIQVY 101                                             150
         BLA   (99)  GDVVINHKGGADATEDVTAVEVDPADRNRVISGEHRIKAWTHFHFPGRGS
     AMY1048  (100)  ADVVFNHKAGADGTELVDAVEVNPSDRNQEISGTYQIQAWTKFDFPGRGN
         BSG  (100)  ADVVFDHKGGADGTEWVDAVEVNPSDRNQEISGTYQIQKAWTKFDFPGRGN
         BAN   (98)  GDVVLNHKAGADATEDVTAVEVNPANRNQETSEEYQIKAWTDFRFPGRGN
    B.sp.K38   (99)  GDVVMNHKMGADFTEAVQAVQVNPTNRWQDISGAYTIDAWTGFDFSGRNN
       AAI-10 (101)  GDVVMNHKGGADFTERVQAVEVNPQNRQEVSGTYQIEAWTGFNFPGRGN
       SP722  (101)  GDVVMNHKGGADATENVLAVEVNPNNRNQEISGDYTIEAWTKFDFPGRGN
       SP690  (101)  GDVVMNHKGGADGTEIVNAVEVNRSNRNQETSGEYAIEAWTKFDFPGRGN
       AA560  (101)  GDVVMNHKGGADATEMVRAVEVNPNNRNQEVSGEYTIEAWTKFDFPGRGN
     Amrk385  (101)  GDVVMNHKGGADGTEWVQAVEVNPSNRNQEVTGEYTIEAWTKFDFPGRGN
    B.sp.707  (101)  GDVVMNHKGGADATEMVRAVEVNPNNRNQEVTGEYTIEAWTRFDFPGRGN
    B.sp.7-7  (101)  GDVVMNHKGGADATEMVRAVEVNPSNRNQEVSGDYTIEAWTRFDFPGRGN
  KSM-AP1378  (101)  GDVVMNHKGGADGTEMVNAVEVNRSNRNQEISGEYTIEAWTKFDFPGRGN
```

FIG. 1A

```
                       151                                           200
         BLA   (149)   TYSDFKWHWYHFDGTDWDESR-KLNRIYKFQG--KAWDWEVSNENGNYDY
     AMY1048   (150)   TYSSFKWRWYHFDGTDWDESR-KLNRIYKFRGTGKAWDWEVDTENGNYDY
         BSG   (150)   TYSSFKWRWYHFDGVDWDESR-KLSRIYKFRGIGKAWDWEVDTENGNYDY
         BAN   (148)   TYSDFKWHWYHFDGADWDESR-KISRIFKFRGEGKAWDWEVSSENGNYDY
    B.sp.K38   (149)   AYSDFKWRWFHFNGVDWDQRY-QENHIFRFAN--TNWNWRVDEENGNYDY
      AAI-10   (151)   QHSSFKWRWYHFDGTDWDQSRQLANRIYKFRGDGKAWDWEVDTENGNYDY
       SP722   (151)   TYSDFKWRWYHFDGVDWDQSRQFQNRIYKFRGDGKAWDWEVDSENGNYDY
       SP690   (151)   NHSSFKWRWYHFDGTDWDQSRQLQNKIYKFRGTGKAWDWEVDTENGNYDY
       AA560   (151)   THSNFKWRWYHFDGVDWDQSRKLNNRIYKFRGDGKGWDWEVDTENGNYDY
     Amrk385   (151)   THSSFKWRWYHFDGTDWDQSRQLNNRIYKFRGTGKAWDWEVDTENGNYDY
    B.sp.707   (151)   THSSFKWRWYHFDGVDWDQSRRLNNRIYKFRGHGKAWDWEVDTENGNYDY
    B.sp.7-7   (151)   THSNFKWRWYHFDGVDWDQSRQLQNRIYKFRGDGKAWDWEVDTENGNYDY
   KSM-AP1378  (151)   THSNFKWRWYHFDGTDWDQSRQLQNKIYKFRGTGKAWDWEVDIENGNYDY 201                                           250
         BLA   (196)   LMYADIDYDHPDVAAEIKRWGTWYANELQLDGFRLDAVKHIKFSFLRDWV
     AMY1048   (199)   LMYADLDMDHPEVVSELKNWGKWYVTTTNIDGFRLDAVKHIKYSFFPDWL
         BSG   (199)   LMYADLDMDHPEVVTELKNWGKWYVNTTNIDGFRLDAVKHIKFSFFPDWL
         BAN   (197)   LMYADVDYDHPDVVAETKKWGIWYANELSLDGFRIDAAKHIKFSFLRDWV
    B.sp.K38   (196)   LLGSNIDFSHPEVQDELKDWGSWFTDELDLDGYRLDAIKHIPFWYTSDWV
      AAI-10   (201)   LMYADVDMDHPEVINELNRWGVWYANTLNLDGFRLDAVKHIKFSFMRDWL
       SP722   (201)   LMYADVDMDHPEVVNELRRWGEWYTNTLNLDGFRIDAVKHIKYSFTRDWL
       SP690   (201)   LMYADVDMDHPEVIHELRNWGVWYTNTLNLDGFRIDAVKHIKYSFTRDWL
       AA560   (201)   LMYADIDMDHPEVVNELRNWGVWYTNTLGLDGFRIDAVKHIKYSFTRDWI
     Amrk385   (201)   LMYADVDMDHPEVINELRRWGVWYTNTLNLDGFRIDAVKHIKYSFTRDWL
    B.sp.707   (201)   LMYADIDMDHPEVVNELRNWGVWYTNTLGLDGFRIDAVKHIKYSFTRDWI
    B.sp.7-7   (201)   LMYADIDMDHPEVVNELRNWGVWYTNTLGLDGFRIGAVKHIKYSFTRDWL
   KSM-AP1378  (201)   LMYADIDMDHPEVINELRNWGVWYTNTLNLDGFRIDAVKHIKYSYTRDWL 251                                           300
         BLA   (246)   NHVREKTGKE-MFTVAEYWQNDLGALENYLNKTNFNHSVFDVPLHYQFHA
     AMY1048   (249)   SYVRTQTQKP-LFAVGEFWSYDISKLHNYITKTNGSMSLFDAPLHNNFYI
         BSG   (249)   SYVRSQTGKP-LFTVGEYWSYDINKLHNYITKTNGTMSLFDAPLHNKFYT
         BAN   (247)   QAVRQATGKE-MFTVAEYWQNNAGKLENYLNKTSFNQSVFDVPLHFNLQA
    B.sp.K38   (246)   RHQRNEADQD-LFVVGEYWKDDVGALEFYLDEMNWEMSLFDVPLNYNFYR
      AAI-10   (251)   GHVRGQTGKN-LFAVAEYWKNDLGALENYLSKTNWTMSAFDVPLHYNLYQ
       SP722   (251)   THVRNATGKE-MFAVAEFWKNDLGALENYLNKTNWHSVFDVPLHYNLYN
       SP690   (251)   THVRNTTGKP-MFAVAEFWKNDLGAIENYLNKTSWNHSVFDVPLHYNLYN
       AA560   (251)   NHVRSATGKN-MFAVAEFWKNDLGAIENYLNKTNWHSVFDVPLHYNLYN
     Amrk385   (251)   NHVRSTTGKNNMFAVAEFWKNDLGAIENYLHKTNWNHSVFDVPLHYNLYN
    B.sp.707   (251)   NHVRSATGKN-MFAVAEFWKNDLGAIENYLQKTNWNHSVFDVPLHYNLYN
    B.sp.7-7   (251)   THVRNTTGKN-MFAVAEFWKNDIGAIENYLSKTNWNHSVFDVPLHYNLYN
   KSM-AP1378  (251)   THVRNTTGKP-MFAVAEFWKNDLAAIENYLNKTSWNHSVFDVPLHYNLYN
```

FIG. 1B

```
              301                                               350
       BLA (295) ASTQGGGYDMRKLLNGTVVSKHPLKAVTFVDNHDTQPGQSLESTVQTWFK
   AMY1048 (298) ASKSGGYFDMRTLLNNTLMKDQPTLAVTLVDNHDTEPGQSLQSWVEPWFK
       BSG (298) ASKSGGAFDMRTLMTNTLMKDQPTLAVTFVDNHDTEPGQALQSWVDPWFK
       BAN (296) ASSQGGGYDMRRLLDGTVVSRHPEKAVTFVENHDTQPGQSLESTVQTWFK
  B.sp.K38 (295) ASQQGGSYDMRNILRGSLVEAHPMHAVTFVDNHDTQPGESLESWVADWFK
    AAI-10 (300) ASNSSGNYDMRNLLNGTLVQRHPSHAVTFVDNHDTQPGEALESFVQGWFK
     SP722 (300) ASNSGGNYDMAKLLNGTVVQKHPMHAVTFVDNHDSQPGESLESFVQEWFK
     SP690 (300) ASNSGGYYDMRNILNGSVVQKHPTHAVTFVDNHDSQPGEALESFVQQWFK
     AA560 (300) ASKSGGNYDMRQIFNGTVVQRHPMHAVTFVDNHDSQPEEALESFVEEWFK
   Amrk385 (301) ASKSGGNYDMRQILNGTVVSKHPIHAVTFVDNHDSQPGEALESFVEAWFK
  B.sp.707 (300) ASKSGGNYDMRNIFNGTVVQRHPSHAVTFVDNHDSQPEEALESFVEEWFK
  B.sp.7-7 (300) ASRSGGNYDMRQIFNGTVVQRHPTHAVTFVDNHDSQPEEALESFVEEWFK
 KSM-AP1378 (300) ASNSGGYFDMRNILNGSVVQKHPIHAVTFVDNHDSQPGEALESFVQSWFK 351                                               400
       BLA (345) PLAYAFILTRESGYPQVFYGDMYGTKGDSQREIPALKHKIEPILKARKQY
   AMY1048 (348) PLAYAFILTRQEGYPCVFYGDYYGIPKYN---IPALKSKLDPLLIARRDY
       BSG (348) PLAYAFILTRQEGYPCVFYGDYYGIPQYN---IPSLKSKIDPLLIARRDY
       BAN (346) PLAYAFILTRESGYPQVFYGDMYGTKGTSPKEIPSLKDNIEPILKARKEY
  B.sp.K38 (345) PLAYATILTREGGYPNVFYGDYYGIPNDN---ISAKKDMIDELLDARQNY
    AAI-10 (350) PLAYATILTREQGYPQVFYGDYYGIPSDG---VPSYRQQIDPLLKARQQY
     SP722 (350) PLAYALILTREQGYPSVFYGDYYGIPTHS---VPAMKAKIDPILEARQNF
     SP690 (350) PLAYALVLTREQGYPSVFYGDYYGIPTHG---VPAMKSKIDPLLQARQTF
     AA560 (350) PLAYALTLTREQGYPSVFYGDYYGIPTHG---VPAMKSKIDPILEARQKY
   Amrk385 (351) PLAYALILTREQGYPSVFYGDYYGIPTHG---VAAMKGKIDPILEARQKY
  B.sp.707 (350) PLAYALTLTREQGYPSVFYGDYYGIPTHG---VPAMRSKIDPILEARQKY
  B.sp.7-7 (350) PLACALTLTRDQGYPSVFYGDYYGIPTHG---VPAMKSKIDPILEARQKY
 KSM-AP1378 (350) PLAYALILTREQGYPSVFYGDYYGIPTHG---VPSMKSKIDPLLQARQTY 401                                               450
       BLA (395) AYGAQHDYFDHHDIVGWTREGDSSVANSGLAALITDGPGGAKRMYVGRQN
   AMY1048 (395) AYGTQHDYIDSADIIGWTREGVAEKANSGLAALITDGPGGSKWMYVGKQH
       BSG (395) AYGTQHDYLDHSDIIGWTREGVTEKPGSGLAALITDGPGGSKWMYVGKQH
       BAN (396) AYGPQHDYIDHPDVIGWTREGDSSAAKSGLAALITDGPGGSKRMYAGLKN
  B.sp.K38 (392) AYGTQHDYFDHWDVVGWTREGSSSRPNSGLATIMSNGPGGSKWMYVGRQN
    AAI-10 (397) AYGRQHDYFDHWDVIGWTREGNASHPNSGLATIMSDGPGGSKWMYVGRQK
     SP722 (397) AYGTQHDYFDHHNIIGWTREGNTTHPNSGLATIMSDGPGGEKWMYVGQNK
     SP690 (397) AYGTQHDYFDHHDIIGWTREGNSSHPNSGLATIMSDGPGGNKWMYVGKNK
     AA560 (397) AYGRQNDYLDHHNIIGWTREGNTAHPNSGLATIMSDGAGGNKWMFVGRNK
   Amrk385 (398) AYGTQHDYLDHHNIIGWTREGNSAHPNSGLATIMSDGPGGSKWMYVGRHK
  B.sp.707 (397) AYGKQNDYLDHHNIIGWTREGNTAHPNSGLATIMSDGAGGSKWMFVGRNK
  B.sp.7-7 (397) AYGKQNDYLDHHNMIGWTREGNTAHPNSGLATIMSDGPGGNKWMYVGRNK
 KSM-AP1378 (397) AYGTQHDYFDHHDIIGWTREGDSSHPNSGLATIMSDGPGGNKWMYVGKHK
```

FIG. 1C

```
                451                                              500
      BLA (445) AGETWHDITGNRSEPVVINSEGWGEFHVNGGSVSIYVQR-----------
  AMY1048 (445) AGKTFYDLTGNRSDTVTINADGWGEFKVNGGSVSIWVPKISTTSQITFTV
      BSG (445) AGKVFYDLTGNRSDTVTINSDGWGEFKVNGGSVSVWVPRKTTVSTIARPI
      BAN (446) AGETWYDITGNRSDTVKIGSDGWGEFHVNDGSVSIYVQK-----------
 B.sp.K38 (442) AGQTWTDLTGNNGASVTINGDGWGEFFTNGGSVSVYVNQ-----------
   AAI-10 (447) AGEVWHDMTGNRSGTVTINQDGWGHFFVNGGSVSVWVKR-----------
    SP722 (447) AGQVWHDITGNKPGTVTINADGWANFSVNGGSVSIWVKR-----------
    SP690 (447) AGQVWRDITGNRTGTVTINADGWGNFSVNGGSVSVWVKQ-----------
    AA560 (447) AGQVWTDITGNRAGTVTINADGWGNFSVNGGSVSIWVNK-----------
   Amrk385 (448) AGQVWRDITGNRTGTVTINADGWGNFSVNGGSVSIWVNK-----------
 B.sp.707 (447) AGQVWSDITGNRTGTVTINADGWGNFSVNGGSVSIWVNK-----------
 B.sp.7-7 (447) AGQVWRDITGNRSGTVTINADGWGNFSVNGGSVSIWVNN-----------
KSM-AP1378 (447) AGQVWRDITGNRSGTVTINADGWGNFTVNGGAVSVWVKQ-----------

501                                              550
      BLA (484) --------------------------------------------------
  AMY1048 (495) NNATTVWGQNVYVVGNISQLGNWDPVHAVQMTPSSYPTWTVTIPLLQGQN
      BSG (495) TTRPWTG---EFVRWTEPRLVAWP--------------------------
      BAN (485) --------------------------------------------------
 B.sp.K38 (481) --------------------------------------------------
   AAI-10 (486) --------------------------------------------------
    SP722 (486) --------------------------------------------------
    SP690 (486) --------------------------------------------------
    AA560 (486) --------------------------------------------------
   Amrk385 (487) --------------------------------------------------
 B.sp.707 (486) --------------------------------------------------
 B.sp.7-7 (486) --------------------------------------------------
KSM-AP1378 (486) --------------------------------------------------

551                                      591
      BLA (484) ---------------------------------------- (SEQ ID NO: 8)
  AMY1048 (545) IQFKFIKKDSAGNVIWEDISNRTYTVPTAASGAYTASWNVP (SEQ ID NO: 13)
      BSG (516) ---------------------------------------- (SEQ ID NO: 6)
      BAN (485) ---------------------------------------- (SEQ ID NO: 10)
 B.sp.K38 (481) ---------------------------------------- (SEQ ID NO: 15)
   AAI-10 (486) ---------------------------------------- (SEQ ID NO: 16)
    SP722 (486) ---------------------------------------- (SEQ ID NO: 3)
    SP690 (486) ---------------------------------------- (SEQ ID NO: 2)
    AA560 (486) ---------------------------------------- (SEQ ID NO: 12)
   Amrk385 (487) ---------------------------------------- (SEQ ID NO: 14)
 B.sp.707 (486) ---------------------------------------- (SEQ ID NO: 19)
 B.sp.7-7 (486) ---------------------------------------- (SEQ ID NO: 18)
KSM-AP1378 (486) ---------------------------------------- (SEQ ID NO: 17)
```

FIG. 1D

SEQUENCE LISTING

```
<160> NUMBER OF SEQ ID NOS: 19

<210> SEQ ID NO 1
<211> LENGTH: 1455
<212> TYPE: DNA
<213> ORGANISM: Bacillus SP690
<220> FEATURE:
<221> NAME/KEY: CDS
<222> LOCATION: (1)..(1455)

<400> SEQUENCE: 1 cat cat aat gga aca aat ggt act atg atg caa tat ttc gaa tgg tat      48
His His Asn Gly Thr Asn Gly Thr Met Met Gln Tyr Phe Glu Trp Tyr
1               5                   10                  15 ttg cca aat gac ggg aat cat tgg aac agg ttg agg gat gac gca gct      96
Leu Pro Asn Asp Gly Asn His Trp Asn Arg Leu Arg Asp Asp Ala Ala
                20                  25                  30
```

| | | | | | | | | | | | | | | | | |
|---|---|---|---|---|---|---|---|---|---|---|---|---|---|---|---|---|
| aac | tta | aag | agt | aaa | ggg | ata | aca | gct | gta | tgg | atc | cca | cct | gca | tgg | 144 |
| Asn | Leu | Lys | Ser | Lys | Gly | Ile | Thr | Ala | Val | Trp | Ile | Pro | Pro | Ala | Trp | |
| | | 35 | | | | | 40 | | | | | 45 | | | | |
| aag | ggg | act | tcc | cag | aat | gat | gta | ggt | tat | gga | gcc | tat | gat | tta | tat | 192 |
| Lys | Gly | Thr | Ser | Gln | Asn | Asp | Val | Gly | Tyr | Gly | Ala | Tyr | Asp | Leu | Tyr | |
| | 50 | | | | | 55 | | | | | 60 | | | | | |
| gat | ctt | gga | gag | ttt | aac | cag | aag | ggg | acg | gtt | cgt | aca | aaa | tat | gga | 240 |
| Asp | Leu | Gly | Glu | Phe | Asn | Gln | Lys | Gly | Thr | Val | Arg | Thr | Lys | Tyr | Gly | |
| 65 | | | | | 70 | | | | | 75 | | | | | 80 | |
| aca | cgc | aac | cag | cta | cag | gct | gcg | gtg | acc | tct | tta | aaa | aat | aac | ggc | 288 |
| Thr | Arg | Asn | Gln | Leu | Gln | Ala | Ala | Val | Thr | Ser | Leu | Lys | Asn | Asn | Gly | |
| | | | | 85 | | | | | 90 | | | | | 95 | | |
| att | cag | gta | tat | ggt | gat | gtc | gtc | atg | aat | cat | aaa | ggt | gga | gca | gat | 336 |
| Ile | Gln | Val | Tyr | Gly | Asp | Val | Val | Met | Asn | His | Lys | Gly | Gly | Ala | Asp | |
| | | | 100 | | | | | 105 | | | | | 110 | | | |
| ggt | acg | gaa | att | gta | aat | gcg | gta | gaa | gtg | aat | cgg | agc | aac | cga | aac | 384 |
| Gly | Thr | Glu | Ile | Val | Asn | Ala | Val | Glu | Val | Asn | Arg | Ser | Asn | Arg | Asn | |
| | | | | 115 | | | | | 120 | | | | | 125 | | |
| cag | gaa | acc | tca | gga | gag | tat | gca | ata | gaa | gcg | tgg | aca | aag | ttt | gat | 432 |
| Gln | Glu | Thr | Ser | Gly | Glu | Tyr | Ala | Ile | Glu | Ala | Trp | Thr | Lys | Phe | Asp | |
| | | 130 | | | | | 135 | | | | | 140 | | | | |
| ttt | cct | gga | aga | gga | aat | aac | cat | tcc | agc | ttt | aag | tgg | cgc | tgg | tat | 480 |
| Phe | Pro | Gly | Arg | Gly | Asn | Asn | His | Ser | Ser | Phe | Lys | Trp | Arg | Trp | Tyr | |
| 145 | | | | | 150 | | | | | 155 | | | | | 160 | |
| cat | ttt | gat | ggg | aca | gat | tgg | gat | cag | tca | cgc | cag | ctt | caa | aac | aaa | 528 |
| His | Phe | Asp | Gly | Thr | Asp | Trp | Asp | Gln | Ser | Arg | Gln | Leu | Gln | Asn | Lys | |
| | | | | 165 | | | | | 170 | | | | | 175 | | |
| ata | tat | aaa | ttc | agg | gga | aca | ggc | aag | gcc | tgg | gac | tgg | gaa | gtc | gat | 576 |
| Ile | Tyr | Lys | Phe | Arg | Gly | Thr | Gly | Lys | Ala | Trp | Asp | Trp | Glu | Val | Asp | |
| | | | 180 | | | | | 185 | | | | | 190 | | | |
| aca | gag | aat | ggc | aac | tat | gac | tat | ctt | atg | tat | gca | gac | gtg | gat | atg | 624 |
| Thr | Glu | Asn | Gly | Asn | Tyr | Asp | Tyr | Leu | Met | Tyr | Ala | Asp | Val | Asp | Met | |
| | | | | 195 | | | | | 200 | | | | | 205 | | |
| gat | cac | cca | gaa | gta | ata | cat | gaa | ctt | aga | aac | tgg | gga | gtg | tgg | tat | 672 |
| Asp | His | Pro | Glu | Val | Ile | His | Glu | Leu | Arg | Asn | Trp | Gly | Val | Trp | Tyr | |
| | | 210 | | | | | 215 | | | | | 220 | | | | |
| acg | aat | aca | ctg | aac | ctt | gat | gga | ttt | aga | ata | gat | gca | gtg | aaa | cat | 720 |
| Thr | Asn | Thr | Leu | Asn | Leu | Asp | Gly | Phe | Arg | Ile | Asp | Ala | Val | Lys | His | |
| 225 | | | | | 230 | | | | | 235 | | | | | 240 | |
| ata | aaa | tat | agc | ttt | acg | aga | gat | tgg | ctt | aca | cat | gtg | cgt | aac | acc | 768 |
| Ile | Lys | Tyr | Ser | Phe | Thr | Arg | Asp | Trp | Leu | Thr | His | Val | Arg | Asn | Thr | |
| | | | | 245 | | | | | 250 | | | | | 255 | | |
| aca | ggt | aaa | cca | atg | ttt | gca | gtg | gct | gag | ttt | tgg | aaa | aat | gac | ctt | 816 |
| Thr | Gly | Lys | Pro | Met | Phe | Ala | Val | Ala | Glu | Phe | Trp | Lys | Asn | Asp | Leu | |
| | | | 260 | | | | | 265 | | | | | 270 | | | |
| ggt | gca | att | gaa | aac | tat | ttg | aat | aaa | aca | agt | tgg | aat | cac | tcg | gtg | 864 |
| Gly | Ala | Ile | Glu | Asn | Tyr | Leu | Asn | Lys | Thr | Ser | Trp | Asn | His | Ser | Val | |
| | | | 275 | | | | | 280 | | | | | 285 | | | |
| ttt | gat | gtt | cct | ctc | cac | tat | aat | ttg | tac | aat | gca | tct | aat | agc | ggt | 912 |
| Phe | Asp | Val | Pro | Leu | His | Tyr | Asn | Leu | Tyr | Asn | Ala | Ser | Asn | Ser | Gly | |
| | | 290 | | | | | 295 | | | | | 300 | | | | |
| ggt | tat | tat | gat | atg | aga | aat | att | tta | aat | ggt | tct | gtg | gtg | caa | aaa | 960 |
| Gly | Tyr | Tyr | Asp | Met | Arg | Asn | Ile | Leu | Asn | Gly | Ser | Val | Val | Gln | Lys | |
| 305 | | | | | 310 | | | | | 315 | | | | | 320 | |
| cat | cca | aca | cat | gcc | gtt | act | ttt | gtt | gat | aac | cat | gat | tct | cag | ccc | 1008 |
| His | Pro | Thr | His | Ala | Val | Thr | Phe | Val | Asp | Asn | His | Asp | Ser | Gln | Pro | |
| | | | | 325 | | | | | 330 | | | | | 335 | | |
| ggg | gaa | gca | ttg | gaa | tcc | ttt | gtt | caa | caa | tgg | ttt | aaa | cca | ctt | gca | 1056 |
| Gly | Glu | Ala | Leu | Glu | Ser | Phe | Val | Gln | Gln | Trp | Phe | Lys | Pro | Leu | Ala | |
| | | | 340 | | | | | 345 | | | | | 350 | | | |

```
                                                        -continued tat gca ttg gtt ctg aca agg gaa caa ggt tat cct tcc gta ttt tat        1104
Tyr Ala Leu Val Leu Thr Arg Glu Gln Gly Tyr Pro Ser Val Phe Tyr
        355                 360                 365 ggg gat tac tac ggt atc cca acc cat ggt gtt ccg gct atg aaa tct        1152
Gly Asp Tyr Tyr Gly Ile Pro Thr His Gly Val Pro Ala Met Lys Ser
370                 375                 380 aaa ata gac cct ctt ctg cag gca cgt caa act ttt gcc tat ggt acg        1200
Lys Ile Asp Pro Leu Leu Gln Ala Arg Gln Thr Phe Ala Tyr Gly Thr
385                 390                 395                 400 cag cat gat tac ttt gat cat cat gat att atc ggt tgg aca aga gag        1248
Gln His Asp Tyr Phe Asp His His Asp Ile Ile Gly Trp Thr Arg Glu
                405                 410                 415 gga aat agc tcc cat cca aat tca ggc ctt gcc acc att atg tca gat        1296
Gly Asn Ser Ser His Pro Asn Ser Gly Leu Ala Thr Ile Met Ser Asp
            420                 425                 430 ggt cca ggt ggt aac aaa tgg atg tat gtg ggg aaa aat aaa gcg gga        1344
Gly Pro Gly Gly Asn Lys Trp Met Tyr Val Gly Lys Asn Lys Ala Gly
        435                 440                 445 caa gtt tgg aga gat att acc gga aat agg aca ggc acc gtc aca att        1392
Gln Val Trp Arg Asp Ile Thr Gly Asn Arg Thr Gly Thr Val Thr Ile
450                 455                 460 aat gca gac gga tgg ggt aat ttc tct gtt aat gga ggg tcc gtt tcg        1440
Asn Ala Asp Gly Trp Gly Asn Phe Ser Val Asn Gly Gly Ser Val Ser
465                 470                 475                 480 gtt tgg gtg aag caa                                                    1455
Val Trp Val Lys Gln
                485

<210> SEQ ID NO 2
<211> LENGTH: 485
<212> TYPE: PRT
<213> ORGANISM: Bacillus SP690

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
```

-continued

```
                180                 185                 190
Thr Glu Asn Gly Asn Tyr Asp Tyr Leu Met Tyr Ala Asp Val Asp Met
            195                 200                 205

Asp His Pro Glu Val Ile His Glu Leu Arg Asn Trp Gly Val Trp Tyr
        210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
            485

<210> SEQ ID NO 3
<211> LENGTH: 1455
<212> TYPE: DNA
<213> ORGANISM: Bacillus SP722
<220> FEATURE:
<221> NAME/KEY: CDS
<222> LOCATION: (1)..(1455)

<400> SEQUENCE: 3 cat cat aat ggg aca aat ggg acg atg atg caa tac ttt gaa tgg cac      48
His His Asn Gly Thr Asn Gly Thr Met Met Gln Tyr Phe Glu Trp His
1               5                  10                  15 ttg cct aat gat ggg aat cac tgg aat aga tta aga gat gat gct agt      96
Leu Pro Asn Asp Gly Asn His Trp Asn Arg Leu Arg Asp Asp Ala Ser
            20                  25                  30 aat cta aga aat aga ggt ata acc gct att tgg att ccg cct gcc tgg     144
```

```
                Asn Leu Arg Asn Arg Gly Ile Thr Ala Ile Trp Ile Pro Ala Trp
                         35                  40                  45 aaa ggg act tcg caa aat gat gtg ggg tat gga gcc tat gat ctt tat       192
Lys Gly Thr Ser Gln Asn Asp Val Gly Tyr Gly Ala Tyr Asp Leu Tyr
         50                  55                  60 gat tta ggg gaa ttt aat caa aag ggg acg gtt cgt act aag tat ggg       240
Asp Leu Gly Glu Phe Asn Gln Lys Gly Thr Val Arg Thr Lys Tyr Gly
 65                  70                  75                  80 aca cgt agt caa ttg gag tct gcc atc cat gct tta aag aat aat ggc       288
Thr Arg Ser Gln Leu Glu Ser Ala Ile His Ala Leu Lys Asn Asn Gly
                 85                  90                  95 gtt caa gtt tat ggg gat gta gtg atg aac cat aaa gga gga gct gat       336
Val Gln Val Tyr Gly Asp Val Val Met Asn His Lys Gly Gly Ala Asp
             100                 105                 110 gct aca gaa aac gtt ctt gct gtc gag gtg aat cca aat aac cgg aat       384
Ala Thr Glu Asn Val Leu Ala Val Glu Val Asn Pro Asn Asn Arg Asn
         115                 120                 125 caa gaa ata tct ggg gac tac aca att gag gct tgg act aag ttt gat       432
Gln Glu Ile Ser Gly Asp Tyr Thr Ile Glu Ala Trp Thr Lys Phe Asp
     130                 135                 140 ttt cca ggg agg ggt aat aca tac tca gac ttt aaa tgg cgt tgg tat       480
Phe Pro Gly Arg Gly Asn Thr Tyr Ser Asp Phe Lys Trp Arg Trp Tyr
145                 150                 155                 160 cat ttc gat ggt gta gat tgg gat caa tca cga caa ttc caa aat cgt       528
His Phe Asp Gly Val Asp Trp Asp Gln Ser Arg Gln Phe Gln Asn Arg
                 165                 170                 175 atc tac aaa ttc cga ggt gat ggt aag gca tgg gat tgg gaa gta gat       576
Ile Tyr Lys Phe Arg Gly Asp Gly Lys Ala Trp Asp Trp Glu Val Asp
             180                 185                 190 tcg gaa aat gga aat tat gat tat tta atg tat gca gat gta gat atg       624
Ser Glu Asn Gly Asn Tyr Asp Tyr Leu Met Tyr Ala Asp Val Asp Met
         195                 200                 205 gat cat ccg gag gta gta aat gag ctt aga aga tgg gga gaa tgg tat       672
Asp His Pro Glu Val Val Asn Glu Leu Arg Arg Trp Gly Glu Trp Tyr
     210                 215                 220 aca aat aca tta aat ctt gat gga ttt agg atc gat gcg gtg aag cat       720
Thr Asn Thr Leu Asn Leu Asp Gly Phe Arg Ile Asp Ala Val Lys His
225                 230                 235                 240 att aaa tat agc ttt aca cgt gat tgg ttg acc cat gta aga aac gca       768
Ile Lys Tyr Ser Phe Thr Arg Asp Trp Leu Thr His Val Arg Asn Ala
                 245                 250                 255 acg gga aaa gaa atg ttt gct gtt gct gaa ttt tgg aaa aat gat tta       816
Thr Gly Lys Glu Met Phe Ala Val Ala Glu Phe Trp Lys Asn Asp Leu
             260                 265                 270 ggt gcc ttg gag aac tat tta aat aaa aca aac tgg aat cat tct gtc       864
Gly Ala Leu Glu Asn Tyr Leu Asn Lys Thr Asn Trp Asn His Ser Val
         275                 280                 285 ttt gat gtc ccc ctt cat tat aat ctt tat aac gcg tca aat agt gga       912
Phe Asp Val Pro Leu His Tyr Asn Leu Tyr Asn Ala Ser Asn Ser Gly
     290                 295                 300 ggc aac tat gac atg gca aaa ctt ctt aat gga acg gtt gtt caa aag       960
Gly Asn Tyr Asp Met Ala Lys Leu Leu Asn Gly Thr Val Val Gln Lys
305                 310                 315                 320 cat cca atg cat gcc gta act ttt gtg gat aat cac gat tct caa cct      1008
His Pro Met His Ala Val Thr Phe Val Asp Asn His Asp Ser Gln Pro
                 325                 330                 335 ggg gaa tca tta gaa tca ttt gta caa gaa tgg ttt aag cca ctt gct      1056
Gly Glu Ser Leu Glu Ser Phe Val Gln Glu Trp Phe Lys Pro Leu Ala
             340                 345                 350
```

```
tat gcg ctt att tta aca aga gaa caa ggc tat ccc tct gtc ttc tat    1104
Tyr Ala Leu Ile Leu Thr Arg Glu Gln Gly Tyr Pro Ser Val Phe Tyr
        355                 360                 365 ggt gac tac tat gga att cca aca cat agt gtc cca gca atg aaa gcc    1152
Gly Asp Tyr Tyr Gly Ile Pro Thr His Ser Val Pro Ala Met Lys Ala
    370                 375                 380 aag att gat cca atc tta gag gcg cgt caa aat ttt gca tat gga aca    1200
Lys Ile Asp Pro Ile Leu Glu Ala Arg Gln Asn Phe Ala Tyr Gly Thr
385                 390                 395                 400 caa cat gat tat ttt gac cat cat aat ata atc gga tgg aca cgt gaa    1248
Gln His Asp Tyr Phe Asp His His Asn Ile Ile Gly Trp Thr Arg Glu
                405                 410                 415 gga aat acc acg cat ccc aat tca gga ctt gcg act atc atg tcg gat    1296
Gly Asn Thr Thr His Pro Asn Ser Gly Leu Ala Thr Ile Met Ser Asp
            420                 425                 430 ggg cca ggg gga gag aaa tgg atg tac gta ggg caa aat aaa gca ggt    1344
Gly Pro Gly Gly Glu Lys Trp Met Tyr Val Gly Gln Asn Lys Ala Gly
        435                 440                 445 caa gtt tgg cat gac ata act gga aat aaa cca gga aca gtt acg atc    1392
Gln Val Trp His Asp Ile Thr Gly Asn Lys Pro Gly Thr Val Thr Ile
    450                 455                 460 aat gca gat gga tgg gct aat ttt tca gta aat gga gga tct gtt tcc    1440
Asn Ala Asp Gly Trp Ala Asn Phe Ser Val Asn Gly Gly Ser Val Ser
465                 470                 475                 480 att tgg gtg aaa cga                                                1455
Ile Trp Val Lys Arg
                485

<210> SEQ ID NO 4
<211> LENGTH: 485
<212> TYPE: PRT
<213> ORGANISM: Bacillus SP722

<400> SEQUENCE: 4

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190
```

```
Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 5
<211> LENGTH: 1548
<212> TYPE: DNA
<213> ORGANISM: Bacillus BSG
<220> FEATURE:
<221> NAME/KEY: CDS
<222> LOCATION: (1)..(1548)

<400> SEQUENCE: 5 gcc gca ccg ttt aac ggc acc atg atg cag tat ttt gaa tgg tac ttg    48
Ala Ala Pro Phe Asn Gly Thr Met Met Gln Tyr Phe Glu Trp Tyr Leu
1               5                   10                  15 ccg gat gat ggc acg tta tgg acc aaa gtg gcc aat gaa gcc aac aac    96
Pro Asp Asp Gly Thr Leu Trp Thr Lys Val Ala Asn Glu Ala Asn Asn
            20                  25                  30 tta tcc agc ctt ggc atc acc gct ctt tgg ctg ccg ccc gct tac aaa    144
Leu Ser Ser Leu Gly Ile Thr Ala Leu Trp Leu Pro Pro Ala Tyr Lys
```

```
                  35                  40                  45
gga aca agc cgc agc gac gta ggg tac gga gta tac gac ttg tat gac       192
Gly Thr Ser Arg Ser Asp Val Gly Tyr Gly Val Tyr Asp Leu Tyr Asp
         50                  55                  60 ctc ggc gaa ttc aat caa aaa ggg acc gtc cgc aca aaa tac gga aca       240
Leu Gly Glu Phe Asn Gln Lys Gly Thr Val Arg Thr Lys Tyr Gly Thr
 65                  70                  75                  80 aaa gct caa tat ctt caa gcc att caa gcc gcc cac gcc gct gga atg       288
Lys Ala Gln Tyr Leu Gln Ala Ile Gln Ala Ala His Ala Ala Gly Met
                     85                  90                  95 caa gtg tac gcc gat gtc gtg ttc gac cat aaa ggc ggc gct gac ggc       336
Gln Val Tyr Ala Asp Val Val Phe Asp His Lys Gly Gly Ala Asp Gly
             100                 105                 110 acg gaa tgg gtg gac gcc gtc gaa gtc aat ccg tcc gac cgc aac caa       384
Thr Glu Trp Val Asp Ala Val Glu Val Asn Pro Ser Asp Arg Asn Gln
         115                 120                 125 gaa atc tcg ggc acc tat caa atc caa gca tgg acg aaa ttt gat ttt       432
Glu Ile Ser Gly Thr Tyr Gln Ile Gln Ala Trp Thr Lys Phe Asp Phe
    130                 135                 140 ccc ggg cgg ggc aac acc tac tcc agc ttt aag tgg cgc tgg tac cat       480
Pro Gly Arg Gly Asn Thr Tyr Ser Ser Phe Lys Trp Arg Trp Tyr His
145                 150                 155                 160 ttt gac ggc gtt gat tgg gac gaa agc cga aaa ttg agc cgc att tac       528
Phe Asp Gly Val Asp Trp Asp Glu Ser Arg Lys Leu Ser Arg Ile Tyr
                 165                 170                 175 aaa ttc cgc ggc atc ggc aaa gcg tgg gat tgg gaa gta gac acg gaa       576
Lys Phe Arg Gly Ile Gly Lys Ala Trp Asp Trp Glu Val Asp Thr Glu
             180                 185                 190 aac gga aac tat gac tac tta atg tat gcc gac ctt gat atg gat cat       624
Asn Gly Asn Tyr Asp Tyr Leu Met Tyr Ala Asp Leu Asp Met Asp His
         195                 200                 205 ccc gaa gtc gtg acc gag ctg aaa aac tgg ggg aaa tgg tat gtc aac       672
Pro Glu Val Val Thr Glu Leu Lys Asn Trp Gly Lys Trp Tyr Val Asn
    210                 215                 220 aca acg aac att gat ggg ttc cgg ctt gat gcc gtc aag cat att aag       720
Thr Thr Asn Ile Asp Gly Phe Arg Leu Asp Ala Val Lys His Ile Lys
225                 230                 235                 240 ttc agt ttt ttt cct gat tgg ttg tcg tat gtg cgt tct cag act ggc       768
Phe Ser Phe Phe Pro Asp Trp Leu Ser Tyr Val Arg Ser Gln Thr Gly
                 245                 250                 255 aag ccg cta ttt acc gtc ggg gaa tat tgg agc tat gac atc aac aag       816
Lys Pro Leu Phe Thr Val Gly Glu Tyr Trp Ser Tyr Asp Ile Asn Lys
             260                 265                 270 ttg cac aat tac att acg aaa aca gac gga acg atg tct ttg ttt gat       864
Leu His Asn Tyr Ile Thr Lys Thr Asp Gly Thr Met Ser Leu Phe Asp
         275                 280                 285 gcc ccg tta cac aac aaa ttt tat acc gct tcc aaa tca ggg ggc gca       912
Ala Pro Leu His Asn Lys Phe Tyr Thr Ala Ser Lys Ser Gly Gly Ala
    290                 295                 300 ttt gat atg cgc acg tta atg acc aat act ctc atg aaa gat caa ccg       960
Phe Asp Met Arg Thr Leu Met Thr Asn Thr Leu Met Lys Asp Gln Pro
305                 310                 315                 320 aca ttg gcc gtc acc ttc gtt gat aat cat gac acc gaa ccc ggc caa      1008
Thr Leu Ala Val Thr Phe Val Asp Asn His Asp Thr Glu Pro Gly Gln
                 325                 330                 335 gcg ctg cag tca tgg gtc gac cca tgg ttc aaa ccg ttg gct tac gcc      1056
Ala Leu Gln Ser Trp Val Asp Pro Trp Phe Lys Pro Leu Ala Tyr Ala
             340                 345                 350 ttt att cta act cgg cag gaa gga tac ccg tgc gtc ttt atg ggt gac      1104
```

```
                Phe Ile Leu Thr Arg Gln Glu Gly Tyr Pro Cys Val Phe Tyr Gly Asp
                                355                 360                 365 tat tat ggc att cca caa tat aac att cct tcg ctg aaa agc aaa atc            1152
Tyr Tyr Gly Ile Pro Gln Tyr Asn Ile Pro Ser Leu Lys Ser Lys Ile
        370                 375                 380 gat ccg ctc ctc atc gcg cgc agg gat tat gct tac gga acg caa cat            1200
Asp Pro Leu Leu Ile Ala Arg Arg Asp Tyr Ala Tyr Gly Thr Gln His
385                 390                 395                 400 gat tat ctt gat cac tcc gac atc atc ggg tgg aca agg gaa ggg ggc            1248
Asp Tyr Leu Asp His Ser Asp Ile Ile Gly Trp Thr Arg Glu Gly Gly
                405                 410                 415 act gaa aaa cca gga tcc gga ctg gcc gca ctg atc acc gat ggg ccg            1296
Thr Glu Lys Pro Gly Ser Gly Leu Ala Ala Leu Ile Thr Asp Gly Pro
            420                 425                 430 gga gga agc aaa tgg atg tac gtt ggc aaa caa cac gct gga aaa gtg            1344
Gly Gly Ser Lys Trp Met Tyr Val Gly Lys Gln His Ala Gly Lys Val
                435                 440                 445 ttc tat gac ctt acc ggc aac cgg agt gac acc gtc acc atc aac agt            1392
Phe Tyr Asp Leu Thr Gly Asn Arg Ser Asp Thr Val Thr Ile Asn Ser
        450                 455                 460 gat gga tgg ggg gaa ttc aaa gtc aat ggc ggt tcg gtt tcg gtt tgg            1440
Asp Gly Trp Gly Glu Phe Lys Val Asn Gly Gly Ser Val Ser Val Trp
465                 470                 475                 480 gtt cct aga aaa acg acc gtt tct acc atc gct cgg ccg atc aca acc            1488
Val Pro Arg Lys Thr Thr Val Ser Thr Ile Ala Arg Pro Ile Thr Thr
                485                 490                 495 cga ccg tgg act ggt gaa ttc gtc cgt tgg acc gaa cca cgg ttg gtg            1536
Arg Pro Trp Thr Gly Glu Phe Val Arg Trp Thr Glu Pro Arg Leu Val
            500                 505                 510 gca tgg cct tga                                                            1548
Ala Trp Pro
        515

<210> SEQ ID NO 6
<211> LENGTH: 515
<212> TYPE: PRT
<213> ORGANISM: Bacillus BSG

<400> SEQUENCE: 6

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
```

```
              145                 150                 155                 160

Phe Asp Gly Val Asp Trp Asp Glu Ser Arg Lys Leu Ser Arg Ile Tyr
                        165                 170                 175

Lys Phe Arg Gly Ile Gly Lys Ala Trp Asp Trp Val Asp Thr Glu
                    180                 185                 190

Asn Gly Asn Tyr Asp Tyr Leu Met Tyr Ala Asp Leu Asp Met Asp His
                    195                 200                 205

Pro Glu Val Val Thr Glu Leu Lys Asn Trp Gly Lys Trp Tyr Val Asn
                210                 215                 220

Thr Thr Asn Ile Asp Gly Phe Arg Leu Asp Ala Val Lys His Ile Lys
        225                 230                 235                 240

Phe Ser Phe Phe Pro Asp Trp Leu Ser Tyr Val Arg Ser Gln Thr Gly
                        245                 250                 255

Lys Pro Leu Phe Thr Val Gly Glu Tyr Trp Ser Tyr Asp Ile Asn Lys
                    260                 265                 270

Leu His Asn Tyr Ile Thr Lys Thr Asp Gly Thr Met Ser Leu Phe Asp
                    275                 280                 285

Ala Pro Leu His Asn Lys Phe Tyr Thr Ala Ser Lys Ser Gly Gly Ala
                290                 295                 300

Phe Asp Met Arg Thr Leu Met Thr Asn Thr Leu Met Lys Asp Gln Pro
        305                 310                 315                 320

Thr Leu Ala Val Thr Phe Val Asp Asn His Asp Thr Glu Pro Gly Gln
                        325                 330                 335

Ala Leu Gln Ser Trp Val Asp Pro Trp Phe Lys Pro Leu Ala Tyr Ala
                    340                 345                 350

Phe Ile Leu Thr Arg Gln Glu Gly Tyr Pro Cys Val Phe Tyr Gly Asp
                    355                 360                 365

Tyr Tyr Gly Ile Pro Gln Tyr Asn Ile Pro Ser Leu Lys Ser Lys Ile
                370                 375                 380

Asp Pro Leu Leu Ile Ala Arg Arg Asp Tyr Ala Tyr Gly Thr Gln His
        385                 390                 395                 400

Asp Tyr Leu Asp His Ser Asp Ile Ile Gly Trp Thr Arg Glu Gly Gly
                        405                 410                 415

Thr Glu Lys Pro Gly Ser Gly Leu Ala Ala Leu Ile Thr Asp Gly Pro
                    420                 425                 430

Gly Gly Ser Lys Trp Met Tyr Val Gly Lys Gln His Ala Gly Lys Val
                    435                 440                 445

Phe Tyr Asp Leu Thr Gly Asn Arg Ser Asp Thr Val Thr Ile Asn Ser
                450                 455                 460

Asp Gly Trp Gly Glu Phe Lys Val Asn Gly Gly Ser Val Ser Val Trp
        465                 470                 475                 480

Val Pro Arg Lys Thr Thr Val Ser Thr Ile Ala Arg Pro Ile Thr Thr
                        485                 490                 495

Arg Pro Trp Thr Gly Glu Phe Val Arg Trp Thr Glu Pro Arg Leu Val
                    500                 505                 510

Ala Trp Pro
                515

<210> SEQ ID NO 7
<211> LENGTH: 1920
<212> TYPE: DNA
<213> ORGANISM: Bacillus licheniformis
<220> FEATURE:
<221> NAME/KEY: CDS
<222> LOCATION: (421)..(1872)
```

<400> SEQUENCE: 7

```
cggaagattg aagtacaaa ataagcaaa agattgtcaa tcatgtcatg agccatgcgg      60
gagacggaaa atcgtctta atgcacgata tttatgcaac gttcgcagat gctgctgaag    120
agattattaa aaagctgaaa gcaaaaggct atcaattggt aactgtatct cagcttgaag    180
aagtgaagaa gcagagaggc tattgaataa atgagtagaa gcgccatatc ggcgcttttc    240
ttttggaaga aaatataggg aaaatggtac ttgttaaaaa ttcggaatat ttatacaaca    300
tcatatgttt cacattgaaa ggggaggaga atcatgaaac aacaaaaacg gctttacgcc    360
cgattgctga cgctgttatt tgcgctcatc ttcttgctgc ctcattctgc agcagcggcg    420
```

| | | |
|---|---|---|
| gca aat ctt aat ggg acg ctg atg cag tat ttt gaa tgg tac atg ccc<br>Ala Asn Leu Asn Gly Thr Leu Met Gln Tyr Phe Glu Trp Tyr Met Pro<br>1               5                   10                  15 | | 468 |
| aat gac ggc caa cat tgg agg cgt ttg caa aac gac tcg gca tat ttg<br>Asn Asp Gly Gln His Trp Arg Arg Leu Gln Asn Asp Ser Ala Tyr Leu<br>            20                  25                  30 | | 516 |
| gct gaa cac ggt att act gcc gtc tgg att ccc ccg gca tat aag gga<br>Ala Glu His Gly Ile Thr Ala Val Trp Ile Pro Pro Ala Tyr Lys Gly<br>        35                  40                  45 | | 564 |
| acg agc caa gcg gat gtg ggc tac ggt gct tac gac ctt tat gat tta<br>Thr Ser Gln Ala Asp Val Gly Tyr Gly Ala Tyr Asp Leu Tyr Asp Leu<br>50                  55                  60 | | 612 |
| ggg gag ttt cat caa aaa ggg acg gtt cgg aca aag tac ggc aca aaa<br>Gly Glu Phe His Gln Lys Gly Thr Val Arg Thr Lys Tyr Gly Thr Lys<br>65                  70                  75                  80 | | 660 |
| gga gag ctg caa tct gcg atc aaa agt ctt cat tcc cgc gac att aac<br>Gly Glu Leu Gln Ser Ala Ile Lys Ser Leu His Ser Arg Asp Ile Asn<br>                85                  90                  95 | | 708 |
| gtt tac ggg gat gtg gtc atc aac cac aaa ggc ggc gct gat gcg acc<br>Val Tyr Gly Asp Val Val Ile Asn His Lys Gly Gly Ala Asp Ala Thr<br>            100                 105                 110 | | 756 |
| gaa gat gta acc gcg gtt gaa gtc gat ccc gct gac cgc aac cgc gta<br>Glu Asp Val Thr Ala Val Glu Val Asp Pro Ala Asp Arg Asn Arg Val<br>        115                 120                 125 | | 804 |
| att tca gga gaa cac cta att aaa gcc tgg aca cat ttt cat ttt ccg<br>Ile Ser Gly Glu His Leu Ile Lys Ala Trp Thr His Phe His Phe Pro<br>130                 135                 140 | | 852 |
| ggg cgc ggc agc aca tac agc gat ttt aaa tgg cat tgg tac cat ttt<br>Gly Arg Gly Ser Thr Tyr Ser Asp Phe Lys Trp His Trp Tyr His Phe<br>145                 150                 155                 160 | | 900 |
| gac gga acc gat tgg gac gag tcc cga aag ctg aac cgc atc tat aag<br>Asp Gly Thr Asp Trp Asp Glu Ser Arg Lys Leu Asn Arg Ile Tyr Lys<br>                165                 170                 175 | | 948 |
| ttt caa gga aag gct tgg gat tgg gaa gtt tcc aat gaa aac ggc aac<br>Phe Gln Gly Lys Ala Trp Asp Trp Glu Val Ser Asn Glu Asn Gly Asn<br>            180                 185                 190 | | 996 |
| tat gat tat ttg atg tat gcc gac atc gat tat gac cat cct gat gtc<br>Tyr Asp Tyr Leu Met Tyr Ala Asp Ile Asp Tyr Asp His Pro Asp Val<br>        195                 200                 205 | | 1044 |
| gca gca gaa att aag aga tgg ggc act tgg tat gcc aat gaa ctg caa<br>Ala Ala Glu Ile Lys Arg Trp Gly Thr Trp Tyr Ala Asn Glu Leu Gln<br>    210                 215                 220 | | 1092 |
| ttg gac ggt ttc cgt ctt gat gct gtc aaa cac att aaa ttt tct ttt<br>Leu Asp Gly Phe Arg Leu Asp Ala Val Lys His Ile Lys Phe Ser Phe<br>225                 230                 235                 240 | | 1140 |
| ttg cgg gat tgg gtt aat cat gtc agg gaa aaa acg ggg aag gaa atg<br>Leu Arg Asp Trp Val Asn His Val Arg Glu Lys Thr Gly Lys Glu Met | | 1188 |

```
                    245                 250                 255
ttt acg gta gct gaa tat tgg cag aat gac ttg ggc gcg ctg gaa aac      1236
Phe Thr Val Ala Glu Tyr Trp Gln Asn Asp Leu Gly Ala Leu Glu Asn
            260                 265                 270 tat ttg aac aaa aca aat ttt aat cat tca gtg ttt gac gtg ccg ctt      1284
Tyr Leu Asn Lys Thr Asn Phe Asn His Ser Val Phe Asp Val Pro Leu
        275                 280                 285 cat tat cag ttc cat gct gca tcg aca cag gga ggc tat gat atg          1332
His Tyr Gln Phe His Ala Ala Ser Thr Gln Gly Gly Tyr Asp Met
    290                 295                 300 agg aaa ttg ctg aac ggt acg gtc gtt tcc aag cat ccg ttg aaa tcg      1380
Arg Lys Leu Leu Asn Gly Thr Val Val Ser Lys His Pro Leu Lys Ser
305                 310                 315                 320 gtt aca ttt gtc gat aac cat gat aca cag ccg ggg caa tcg ctt gag      1428
Val Thr Phe Val Asp Asn His Asp Thr Gln Pro Gly Gln Ser Leu Glu
                325                 330                 335 tcg act gtc caa aca tgg ttt aag ccg ctt gct tac gct ttt att ctc      1476
Ser Thr Val Gln Thr Trp Phe Lys Pro Leu Ala Tyr Ala Phe Ile Leu
            340                 345                 350 aca agg gaa tct gga tac cct cag gtt ttc tac ggg gat atg tac ggg      1524
Thr Arg Glu Ser Gly Tyr Pro Gln Val Phe Tyr Gly Asp Met Tyr Gly
        355                 360                 365 acg aaa gga gac tcc cag cgc gaa att cct gcc ttg aaa cac aaa att      1572
Thr Lys Gly Asp Ser Gln Arg Glu Ile Pro Ala Leu Lys His Lys Ile
    370                 375                 380 gaa ccg atc tta aaa gcg aga aaa cag tat gcg tac gga gca cag cat      1620
Glu Pro Ile Leu Lys Ala Arg Lys Gln Tyr Ala Tyr Gly Ala Gln His
385                 390                 395                 400 gat tat ttc gac cac cat gac att gtc ggc tgg aca agg gaa ggc gac      1668
Asp Tyr Phe Asp His His Asp Ile Val Gly Trp Thr Arg Glu Gly Asp
                405                 410                 415 agc tcg gtt gca aat tca ggt ttg gcg gca tta ata aca gac gga ccc      1716
Ser Ser Val Ala Asn Ser Gly Leu Ala Ala Leu Ile Thr Asp Gly Pro
            420                 425                 430 ggt ggg gca aag cga atg tat gtc ggc cgg caa aac gcc ggt gag aca      1764
Gly Gly Ala Lys Arg Met Tyr Val Gly Arg Gln Asn Ala Gly Glu Thr
        435                 440                 445 tgg cat gac att acc gga aac cgt tcg gag ccg gtt gtc atc aat tcg      1812
Trp His Asp Ile Thr Gly Asn Arg Ser Glu Pro Val Val Ile Asn Ser
    450                 455                 460 gaa ggc tgg gga gag ttt cac gta aac ggc ggg tcg gtt tca att tat      1860
Glu Gly Trp Gly Glu Phe His Val Asn Gly Gly Ser Val Ser Ile Tyr
465                 470                 475                 480 gtt caa aga tag aagagcagag aggacggatt tcctgaagga aatccgtttt          1912
Val Gln Arg tttatttt                                                              1920

<210> SEQ ID NO 8
<211> LENGTH: 483
<212> TYPE: PRT
<213> ORGANISM: Bacillus licheniformis

<400> SEQUENCE: 8

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45
```

```
Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Ala Asp Ala Thr
            100                 105                 110

Glu Asp Val Thr Ala Val Glu Val Asp Pro Ala Asp Arg Asn Arg Val
            115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
                180                 185                 190

Tyr Asp Tyr Leu Met Tyr Ala Asp Ile Asp Tyr Asp His Pro Asp Val
            195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
    275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
    435                 440                 445

Trp His Asp Ile Thr Gly Asn Arg Ser Glu Pro Val Val Ile Asn Ser
    450                 455                 460
```

```
                             Glu Gly Trp Gly Glu Phe His Val Asn Gly Gly Ser Val Ser Ile Tyr
                             465                 470                 475                 480

Val Gln Arg

<210> SEQ ID NO 9
<211> LENGTH: 2084
<212> TYPE: DNA
<213> ORGANISM: Bacillus BAN
<220> FEATURE:
<221> NAME/KEY: CDS
<222> LOCATION: (343)..(1794)

<400> SEQUENCE: 9
gccccgcaca tacgaaaaga ctggctgaaa acattgagcc tttgatgact gatgatttgg        60
ctgaagaagt ggatcgattg tttgagaaaa gaagaagacc ataaaaatac cttgtctgtc       120
atcagacagg gtattttta tgctgtccag actgtccgct gtgtaaaaat aaggaataaa        180 gggggttgt tattatttta ctgatatgta aatataatt tgtataagaa atgagaggg         240 agaggaaaca tgattcaaaa acgaaagcgg acagtttcgt tcagacttgt gcttatgtgc       300
acgctgttat ttgtcagttt gccgattaca aaacatcag cc gta aat ggc acg          354
                                                Val Asn Gly Thr
                                                  1 ctg atg cag tat ttt gaa tgg tat acg ccg aac gac ggc cag cat tgg        402
Leu Met Gln Tyr Phe Glu Trp Tyr Thr Pro Asn Asp Gly Gln His Trp
 5              10                  15                  20 aaa cga ttg cag aat gat gcg gaa cat tta tcg gat atc gga atc act        450
Lys Arg Leu Gln Asn Asp Ala Glu His Leu Ser Asp Ile Gly Ile Thr
                 25                  30                  35 gcc gtc tgg att cct ccc gca tac aaa gga ttg agc caa tcc gat aac        498
Ala Val Trp Ile Pro Pro Ala Tyr Lys Gly Leu Ser Gln Ser Asp Asn
         40                  45                  50 gga tac gga cct tat gat ttg tat gat tta gga gaa ttc cag caa aaa        546
Gly Tyr Gly Pro Tyr Asp Leu Tyr Asp Leu Gly Glu Phe Gln Gln Lys
 55                  60                  65 ggg acg gtc aga acg aaa tac ggc aca aaa tca gag ctt caa gat gcg        594
Gly Thr Val Arg Thr Lys Tyr Gly Thr Lys Ser Glu Leu Gln Asp Ala
 70                  75                  80 atc ggc tca ctg cat tcc cgg aac gtc caa gta tac gga gat gtg gtt        642
Ile Gly Ser Leu His Ser Arg Asn Val Gln Val Tyr Gly Asp Val Val
85                  90                  95                 100 ttg aat cat aag gct ggt gct gat gca aca gaa gat gta act gcc gtc        690
Leu Asn His Lys Ala Gly Ala Asp Ala Thr Glu Asp Val Thr Ala Val
                105                 110                 115 gaa gtc aat ccg gcc aat aga aat cag gaa act tcg gag gaa tat caa        738
Glu Val Asn Pro Ala Asn Arg Asn Gln Glu Thr Ser Glu Glu Tyr Gln
         120                 125                 130 atc aaa gcg tgg acg gat ttt cgt ttt ccg ggc cgt gga aac acg tac        786
Ile Lys Ala Trp Thr Asp Phe Arg Phe Pro Gly Arg Gly Asn Thr Tyr
 135                 140                 145 agt gat ttt aaa tgg cat tgg tat cat ttc gac gga gcg gac tgg gat        834
Ser Asp Phe Lys Trp His Trp Tyr His Phe Asp Gly Ala Asp Trp Asp
         150                 155                 160 gaa tcc cgg aag atc agc cgc atc ttt aag ttt cgt ggg gaa gga aaa        882
Glu Ser Arg Lys Ile Ser Arg Ile Phe Lys Phe Arg Gly Glu Gly Lys
165                 170                 175                 180 gcg tgg gat tgg gaa gta tca agt gaa aac ggc aac tat gac tat tta        930
Ala Trp Asp Trp Glu Val Ser Ser Glu Asn Gly Asn Tyr Asp Tyr Leu
                185                 190                 195 atg tat gct gat gtt gac tac gac cac cct gat gtc gtg gca gag aca        978
Met Tyr Ala Asp Val Asp Tyr Asp His Pro Asp Val Val Ala Glu Thr
```

|     |     |     |     |     |     |     |     |     |     |     |     |      |
|-----|-----|-----|-----|-----|-----|-----|-----|-----|-----|-----|-----|------|
| Met | Tyr | Ala | Asp | Val | Asp | Tyr | Asp | His | Pro | Asp | Val | Val | Ala | Glu | Thr |
|     |     | 200 |     |     |     | 205 |     |     |     | 210 |     |      |

```
aaa aaa tgg ggt atc tgg tat gcg aat gaa ctg tca tta gac ggc ttc    1026
Lys Lys Trp Gly Ile Trp Tyr Ala Asn Glu Leu Ser Leu Asp Gly Phe
        215                 220                 225 cgt att gat gcc gcc aaa cat att aaa ttt tca ttt ctg cgt gat tgg    1074
Arg Ile Asp Ala Ala Lys His Ile Lys Phe Ser Phe Leu Arg Asp Trp
        230                 235                 240 gtt cag gcg gtc aga cag gcg acg gga aaa gaa atg ttt acg gtt gcg    1122
Val Gln Ala Val Arg Gln Ala Thr Gly Lys Glu Met Phe Thr Val Ala
245                 250                 255                 260 gag tat tgg cag aat aat gcc ggg aaa ctc gaa aac tac ttg aat aaa    1170
Glu Tyr Trp Gln Asn Asn Ala Gly Lys Leu Glu Asn Tyr Leu Asn Lys
                265                 270                 275 aca agc ttt aat caa tcc gtg ttt gat gtt ccg ctt cat ttc aat tta    1218
Thr Ser Phe Asn Gln Ser Val Phe Asp Val Pro Leu His Phe Asn Leu
        280                 285                 290 cag gcg gct tcc tca caa gga ggc gga tat gat atg agg cgt ttg ctg    1266
Gln Ala Ala Ser Ser Gln Gly Gly Gly Tyr Asp Met Arg Arg Leu Leu
        295                 300                 305 gac ggt acc gtt gtg tcc agg cat ccg gaa aag gcg gtt aca ttt gtt    1314
Asp Gly Thr Val Val Ser Arg His Pro Glu Lys Ala Val Thr Phe Val
310                 315                 320 gaa aat cat gac aca cag ccg gga cag tca ttg gaa tcg aca gtc caa    1362
Glu Asn His Asp Thr Gln Pro Gly Gln Ser Leu Glu Ser Thr Val Gln
325                 330                 335                 340 act tgg ttt aaa ccg ctt gca tac gcc ttt att ttg aca aga gaa tcc    1410
Thr Trp Phe Lys Pro Leu Ala Tyr Ala Phe Ile Leu Thr Arg Glu Ser
                345                 350                 355 ggt tat cct cag gtg ttc tat ggg gat atg tac ggg aca aaa ggg aca    1458
Gly Tyr Pro Gln Val Phe Tyr Gly Asp Met Tyr Gly Thr Lys Gly Thr
                360                 365                 370 tcg cca aag gaa att ccc tca ctg aaa gat aat ata gag ccg att tta    1506
Ser Pro Lys Glu Ile Pro Ser Leu Lys Asp Asn Ile Glu Pro Ile Leu
        375                 380                 385 aaa gcg cgt aag gag tac gca tac ggg ccc cag cac gat tat att gac    1554
Lys Ala Arg Lys Glu Tyr Ala Tyr Gly Pro Gln His Asp Tyr Ile Asp
        390                 395                 400 cac ccg gat gtg atc gga tgg acg agg gaa ggt gac agc tcc gcc gcc    1602
His Pro Asp Val Ile Gly Trp Thr Arg Glu Gly Asp Ser Ser Ala Ala
405                 410                 415                 420 aaa tca ggt ttg gcc gct tta atc acg gac gga ccc ggc gga tca aag    1650
Lys Ser Gly Leu Ala Ala Leu Ile Thr Asp Gly Pro Gly Gly Ser Lys
                425                 430                 435 cgg atg tat gcc ggc ctg aaa aat gcc ggc gag aca tgg tat gac ata    1698
Arg Met Tyr Ala Gly Leu Lys Asn Ala Gly Glu Thr Trp Tyr Asp Ile
        440                 445                 450 acg ggc aac cgt tca gat act gta aaa atc gga tct gac ggc tgg gga    1746
Thr Gly Asn Arg Ser Asp Thr Val Lys Ile Gly Ser Asp Gly Trp Gly
        455                 460                 465 gag ttt cat gta aac gat ggg tcc gtc tcc att tat gtt cag aaa taa    1794
Glu Phe His Val Asn Asp Gly Ser Val Ser Ile Tyr Val Gln Lys
        470                 475                 480 ggtaataaaa aaacacctcc aagctgagtg cgggtatcag cttggaggtg cgtttatttt    1854
ttcagccgta tgacaaggtc ggcatcaggt gtgacaaata cggtatgctg gctgtcatag    1914
gtgacaaatc cgggttttgc gccgtttggc ttttcacat gtctgatttt tgtataatca    1974
acaggcacgg agccggaatc tttcgccttg gaaaaataag cggcgatcgt agctgcttcc    2034
```
aatatggatt gttcatcggg atcgctgctt ttaatcacaa cgtgggatcc 2084

<210> SEQ ID NO 10
<211> LENGTH: 483
<212> TYPE: PRT
<213> ORGANISM: Bacillus BAN

<400> SEQUENCE: 10

```
Val Asn Gly Thr Leu Met Gln Tyr Phe Glu Trp Tyr Thr Pro Asn Asp
 1               5                  10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365
```

```
Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
                420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
450                 455                 460

Asp Gly Trp Gly Glu Phe His Val Asn Asp Gly Ser Val Ser Ile Tyr
465                 470                 475                 480

Val Gln Lys

<210> SEQ ID NO 11
<211> LENGTH: 1458
<212> TYPE: DNA
<213> ORGANISM: Bacillus AA560
<220> FEATURE:
<221> NAME/KEY: CDS
<222> LOCATION: (1)..(1458)

<400> SEQUENCE: 11 cac cat aat ggt acg aac ggc aca atg atg cag tac ttt gaa tgg tat        48
His His Asn Gly Thr Asn Gly Thr Met Met Gln Tyr Phe Glu Trp Tyr
1               5                   10                  15 cta cca aat gac gga aac cat tgg aat aga tta agg tct gat gca agt        96
Leu Pro Asn Asp Gly Asn His Trp Asn Arg Leu Arg Ser Asp Ala Ser
                20                  25                  30 aac cta aaa gat aaa ggg atc tca gcg gtt tgg att cct cct gca tgg       144
Asn Leu Lys Asp Lys Gly Ile Ser Ala Val Trp Ile Pro Pro Ala Trp
            35                  40                  45 aag ggt gcc tct caa aat gat gtg ggg tat ggt gct tat gat ctg tat       192
Lys Gly Ala Ser Gln Asn Asp Val Gly Tyr Gly Ala Tyr Asp Leu Tyr
        50                  55                  60 gat tta gga gaa ttc aat caa aaa gga acc att cgt aca aaa tat gga       240
Asp Leu Gly Glu Phe Asn Gln Lys Gly Thr Ile Arg Thr Lys Tyr Gly
65                  70                  75                  80 acg cgc aat cag tta caa gct gca gtt aac gcc ttg aaa agt aat gga       288
Thr Arg Asn Gln Leu Gln Ala Ala Val Asn Ala Leu Lys Ser Asn Gly
                85                  90                  95 att caa gtg tat ggc gat gtt gta atg aat cat aaa ggg gga gca gac       336
Ile Gln Val Tyr Gly Asp Val Val Met Asn His Lys Gly Gly Ala Asp
            100                 105                 110 gct acc gaa atg gtt agg gca gtt gaa gta aac ccg aat aat aga aat       384
Ala Thr Glu Met Val Arg Ala Val Glu Val Asn Pro Asn Asn Arg Asn
        115                 120                 125 caa gaa gtg tcc ggt gaa tat aca att gag gct tgg aca aag ttt gac       432
Gln Glu Val Ser Gly Glu Tyr Thr Ile Glu Ala Trp Thr Lys Phe Asp
    130                 135                 140 ttt cca gga cga ggt aat act cat tca aac ttc aaa tgg aga tgg tat       480
Phe Pro Gly Arg Gly Asn Thr His Ser Asn Phe Lys Trp Arg Trp Tyr
145                 150                 155                 160 cac ttt gat gga gta gat tgg gat cag tca cgt aag ctg aac aat cga       528
His Phe Asp Gly Val Asp Trp Asp Gln Ser Arg Lys Leu Asn Asn Arg
                165                 170                 175 att tat aaa ttt aga ggt gat gga aaa ggg tgg gat tgg gaa gtc gat       576
Ile Tyr Lys Phe Arg Gly Asp Gly Lys Gly Trp Asp Trp Glu Val Asp
```

```
Ile Tyr Lys Phe Arg Gly Asp Gly Lys Gly Trp Asp Trp Glu Val Asp
            180                 185                 190 aca gaa aac ggt aac tat gat tac cta atg tat gca gat att gac atg      624
Thr Glu Asn Gly Asn Tyr Asp Tyr Leu Met Tyr Ala Asp Ile Asp Met
            195                 200                 205 gat cac cca gag gta gtg aat gag cta aga aat tgg ggt gtt tgg tat      672
Asp His Pro Glu Val Val Asn Glu Leu Arg Asn Trp Gly Val Trp Tyr
210                 215                 220 acg aat aca tta ggc ctt gat ggt ttt aga ata gat gca gta aaa cat      720
Thr Asn Thr Leu Gly Leu Asp Gly Phe Arg Ile Asp Ala Val Lys His
225                 230                 235                 240 ata aaa tac agc ttt act cgt gat tgg att aat cat gtt aga agt gca      768
Ile Lys Tyr Ser Phe Thr Arg Asp Trp Ile Asn His Val Arg Ser Ala
            245                 250                 255 act ggc aaa aat atg ttt gcg gtt gcg gaa ttt tgg aaa aat gat tta      816
Thr Gly Lys Asn Met Phe Ala Val Ala Glu Phe Trp Lys Asn Asp Leu
            260                 265                 270 ggt gct att gaa aac tat tta aac aaa aca aac tgg aac cat tca gtc      864
Gly Ala Ile Glu Asn Tyr Leu Asn Lys Thr Asn Trp Asn His Ser Val
            275                 280                 285 ttt gat gtt ccg ctg cac tat aac ctc tat aat gct tca aaa agc gga      912
Phe Asp Val Pro Leu His Tyr Asn Leu Tyr Asn Ala Ser Lys Ser Gly
290                 295                 300 ggg aat tat gat atg agg caa ata ttt aat ggt aca gtc gtg caa aga      960
Gly Asn Tyr Asp Met Arg Gln Ile Phe Asn Gly Thr Val Val Gln Arg
305                 310                 315                 320 cat cca atg cat gct gtt aca ttt gtt gat aat cat gat tcg caa cct     1008
His Pro Met His Ala Val Thr Phe Val Asp Asn His Asp Ser Gln Pro
            325                 330                 335 gaa gaa gct tta gag tct ttt gtt gaa gaa tgg ttc aaa cca tta gcg     1056
Glu Glu Ala Leu Glu Ser Phe Val Glu Glu Trp Phe Lys Pro Leu Ala
            340                 345                 350 tat gct ttg aca tta aca cgt gaa caa ggc tac cct tct gta ttt tat     1104
Tyr Ala Leu Thr Leu Thr Arg Glu Gln Gly Tyr Pro Ser Val Phe Tyr
            355                 360                 365 gga gat tat tat ggc att cca acg cat ggt gta cca gcg atg aaa tcg     1152
Gly Asp Tyr Tyr Gly Ile Pro Thr His Gly Val Pro Ala Met Lys Ser
370                 375                 380 aaa att gac ccg att cta gaa gcg cgt caa aag tat gca tat gga aga     1200
Lys Ile Asp Pro Ile Leu Glu Ala Arg Gln Lys Tyr Ala Tyr Gly Arg
385                 390                 395                 400 caa aat gac tac tta gac cat cat aat atc atc ggt tgg aca cgt gaa     1248
Gln Asn Asp Tyr Leu Asp His His Asn Ile Ile Gly Trp Thr Arg Glu
            405                 410                 415 ggg aat aca gca cac ccc aac tcc ggt tta gct act atc atg tcc gat     1296
Gly Asn Thr Ala His Pro Asn Ser Gly Leu Ala Thr Ile Met Ser Asp
            420                 425                 430 ggg gca gga gga aat aag tgg atg ttt gtt ggg cgt aat aaa gct ggt     1344
Gly Ala Gly Gly Asn Lys Trp Met Phe Val Gly Arg Asn Lys Ala Gly
            435                 440                 445 caa gtt tgg acc gat atc act gga aat cgt gca ggt act gtt acg att     1392
Gln Val Trp Thr Asp Ile Thr Gly Asn Arg Ala Gly Thr Val Thr Ile
            450                 455                 460 aat gct gat gga tgg ggt aat ttt tct gta aat gga gga tca gtt tct     1440
Asn Ala Asp Gly Trp Gly Asn Phe Ser Val Asn Gly Gly Ser Val Ser
465                 470                 475                 480 att tgg gta aac aaa taa                                              1458
Ile Trp Val Asn Lys
            485
```

<210> SEQ ID NO 12
<211> LENGTH: 485
<212> TYPE: PRT
<213> ORGANISM: Bacillus AA560

<400> SEQUENCE: 12

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
370                 375                 380
```

```
Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
        420                 425                 430

Gly Ala Gly Gly Asn Lys Trp Met Phe Val Gly Arg Asn Lys Ala Gly
    435                 440                 445

Gln Val Trp Thr Asp Ile Thr Gly Asn Arg Ala Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 13
<211> LENGTH: 586
<212> TYPE: PRT
<213> ORGANISM: Bacillus AMY1048

<400> SEQUENCE: 13

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
        35                  40                  45

Lys Gly Thr Ser Ser Ser Asp Val Gly Tyr Gly Val Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
        115                 120                 125

Gln Glu Ile Ser Gly Thr Tyr Gln Ile Gln Ala Trp Thr Lys Phe Asp
130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
    210                 215                 220

Thr Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Val Arg Thr Gln Thr
                245                 250                 255

Gln Lys Pro Leu Phe Ala Val Gly Glu Phe Trp Ser Tyr Asp Ile Ser
```

```
            260                 265                 270
Lys Leu His Asn Tyr Ile Thr Lys Thr Asn Gly Ser Met Ser Leu Phe
            275                 280                 285

Asp Ala Pro Leu His Asn Asn Phe Tyr Ile Ala Ser Lys Ser Gly Gly
            290                 295                 300

Tyr Phe Asp Met Arg Thr Leu Leu Asn Asn Thr Leu Met Lys Asp Gln
305                 310                 315                 320

Pro Thr Leu Ala Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Ala Leu Lys Ser Lys
            370                 375                 380

Leu Asp Pro Leu Leu Ile Ala Arg Arg Asp Tyr Ala Tyr Gly Thr Gln
385                 390                 395                 400

His Asp Tyr Ile Asp Ser Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
            435                 440                 445

Thr Phe Tyr Asp Leu Thr Gly Asn Arg Ser Asp Thr Val Thr Ile Asn
            450                 455                 460

Ala Asp Gly Trp Gly Glu Phe Lys Val Asn Gly Gly Ser Val Ser Ile
465                 470                 475                 480

Trp Val Pro Lys Ile Ser Thr Ser Gln Ile Thr Phe Thr Val Asn
                485                 490                 495

Asn Ala Thr Thr Val Trp Gly Gln Asn Val Tyr Val Gly Asn Ile
            500                 505                 510

Ser Gln Leu Gly Asn Trp Asp Pro Val His Ala Val Gln Met Thr Pro
            515                 520                 525

Ser Ser Tyr Pro Thr Trp Thr Val Thr Ile Pro Leu Leu Gln Gly Gln
            530                 535                 540

Asn Ile Gln Phe Lys Phe Ile Lys Lys Asp Ser Ala Gly Asn Val Ile
545                 550                 555                 560

Trp Glu Asp Ile Ser Asn Arg Thr Tyr Thr Val Pro Thr Ala Ala Ser
                565                 570                 575

Gly Ala Tyr Thr Ala Ser Trp Asn Val Pro
            580                 585

<210> SEQ ID NO 14
<211> LENGTH: 486
<212> TYPE: PRT
<213> ORGANISM: Bacillus AMRK385

<400> SEQUENCE: 14

His His Asn Gly Thr Asn Gly Thr Met Met Gln Tyr Phe Glu Trp His
1               5                   10                  15

Leu Pro Asn Asp Gly Gln His Trp Asn Arg Leu Arg Asn Asp Ala Ala
            20                  25                  30

Asn Leu Lys Asn Leu Gly Ile Thr Ala Val Trp Ile Pro Pro Ala Trp
        35                  40                  45
```

-continued

```
Lys Gly Thr Ser Gln Asn Asp Val Gly Tyr Gly Ala Tyr Asp Leu Tyr
 50                  55                  60
Asp Leu Gly Glu Phe Asn Gln Lys Gly Thr Ile Arg Thr Lys Tyr Gly
 65                  70                  75                  80
Thr Arg Ser Gln Leu Gln Ser Ala Ile Ala Ser Leu Gln Asn Asn Gly
                 85                  90                  95
Ile Gln Val Tyr Gly Asp Val Val Met Asn His Lys Gly Gly Ala Asp
            100                 105                 110
Gly Thr Glu Trp Val Gln Ala Val Glu Val Asn Pro Ser Asn Arg Asn
        115                 120                 125
Gln Glu Val Thr Gly Glu Tyr Thr Ile Glu Ala Trp Thr Lys Phe Asp
130                 135                 140
Phe Pro Gly Arg Gly Asn Thr His Ser Ser Phe Lys Trp Arg Trp Tyr
145                 150                 155                 160
His Phe Asp Gly Thr Asp Trp Asp Gln Ser Arg Gln Leu Asn Asn Arg
                165                 170                 175
Ile Tyr Lys Phe Arg Gly Thr Gly Lys Ala Trp Asp Trp Glu Val Asp
            180                 185                 190
Thr Glu Asn Gly Asn Tyr Asp Tyr Leu Met Tyr Ala Asp Val Asp Met
        195                 200                 205
Asp His Pro Glu Val Ile Asn Glu Leu Arg Arg Trp Gly Val Trp Tyr
210                 215                 220
Thr Asn Thr Leu Asn Leu Asp Gly Phe Arg Ile Asp Ala Val Lys His
225                 230                 235                 240
Ile Lys Tyr Ser Phe Thr Arg Asp Trp Leu Asn His Val Arg Ser Thr
                245                 250                 255
Thr Gly Lys Asn Asn Met Phe Ala Val Ala Glu Phe Trp Lys Asn Asp
            260                 265                 270
Leu Gly Ala Ile Glu Asn Tyr Leu His Lys Thr Asn Trp Asn His Ser
        275                 280                 285
Val Phe Asp Val Pro Leu His Tyr Asn Leu Tyr Asn Ala Ser Lys Ser
290                 295                 300
Gly Gly Asn Tyr Asp Met Arg Gln Ile Leu Asn Gly Thr Val Val Ser
305                 310                 315                 320
Lys His Pro Ile His Ala Val Thr Phe Val Asp Asn His Asp Ser Gln
                325                 330                 335
Pro Gly Glu Ala Leu Glu Ser Phe Val Glu Ala Trp Phe Lys Pro Leu
            340                 345                 350
Ala Tyr Ala Leu Ile Leu Thr Arg Glu Gln Gly Tyr Pro Ser Val Phe
        355                 360                 365
Tyr Gly Asp Tyr Tyr Gly Ile Pro Thr His Gly Val Ala Ala Met Lys
370                 375                 380
Gly Lys Ile Asp Pro Ile Leu Glu Ala Arg Gln Lys Tyr Ala Tyr Gly
385                 390                 395                 400
Thr Gln His Asp Tyr Leu Asp His His Asn Ile Ile Gly Trp Thr Arg
                405                 410                 415
Glu Gly Asn Ser Ala His Pro Asn Ser Gly Leu Ala Thr Ile Met Ser
            420                 425                 430
Asp Gly Pro Gly Gly Ser Lys Trp Met Tyr Val Gly Arg His Lys Ala
        435                 440                 445
Gly Gln Val Trp Arg Asp Ile Thr Gly Asn Arg Thr Gly Thr Val Thr
450                 455                 460
Ile Asn Ala Asp Gly Trp Gly Asn Phe Ser Val Asn Gly Gly Ser Val
```

```
                465                 470                 475                 480
Ser Ile Trp Val Asn Lys
                485

<210> SEQ ID NO 15
<211> LENGTH: 480
<212> TYPE: PRT
<213> ORGANISM: Bacillus SP.K38

<400> SEQUENCE: 15

Asp Gly Leu Asn Gly Thr Met Met Gln Tyr Tyr Glu Trp His Leu Glu
1               5                   10                  15

Asn Asp Gly Gln His Trp Asn Arg Leu His Asp Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350
```

```
Thr Arg Glu Gly Gly Tyr Pro Asn Val Phe Tyr Gly Asp Tyr Tyr Gly
            355                 360                 365

Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
    435                 440                 445

Leu Thr Gly Asn Asn Gly Ala Ser Val Thr Ile Asn Gly Asp Gly Trp
450                 455                 460

Gly Glu Phe Phe Thr Asn Gly Gly Ser Val Ser Val Tyr Val Asn Gln
465                 470                 475                 480

<210> SEQ ID NO 16
<211> LENGTH: 485
<212> TYPE: PRT
<213> ORGANISM: Bacillus AAI-10

<400> SEQUENCE: 16

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255
```

```
Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
            275                 280                 285

Phe Asp Val Pro Leu His Tyr Asn Leu Tyr Gln Ala Ser Asn Ser Ser
290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
            355                 360                 365

Gly Asp Tyr Tyr Gly Ile Pro Ser Asp Gly Val Pro Ser Tyr Arg Gln
370                 375                 380

Gln Ile Asp Pro Leu Leu Lys Ala Arg Gln Gln Tyr Ala Tyr Gly Arg
385                 390                 395                 400

Gln His Asp Tyr Phe Asp His Trp Asp Val Ile Gly Trp Thr Arg Glu
                405                 410                 415

Gly Asn Ala Ser His Pro Asn Ser Gly Leu Ala Thr Ile Met Ser Asp
            420                 425                 430

Gly Pro Gly Gly Ser Lys Trp Met Tyr Val Gly Arg Gln Lys Ala Gly
            435                 440                 445

Glu Val Trp His Asp Met Thr Gly Asn Arg Ser Gly Thr Val Thr Ile
            450                 455                 460

Asn Gln Asp Gly Trp Gly His Phe Phe Val Asn Gly Gly Ser Val Ser
465                 470                 475                 480

Val Trp Val Lys Arg
            485

<210> SEQ ID NO 17
<211> LENGTH: 485
<212> TYPE: PRT
<213> ORGANISM: Bacillus KSM-AP1378

<400> SEQUENCE: 17

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
            85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
            115                 120                 125

Gln Glu Ile Ser Gly Glu Tyr Thr Ile Glu Ala Trp Thr Lys Phe Asp
```

```
                130                 135                 140
Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
                180                 185                 190

Ile Glu Asn Gly Asn Tyr Asp Tyr Leu Met Tyr Ala Asp Ile Asp Met
                195                 200                 205

Asp His Pro Glu Val Ile Asn Glu Leu Arg Asn Trp Gly Val Trp Tyr
                210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
                245                 250                 255

Thr Gly Lys Pro Met Phe Ala Val Ala Glu Phe Trp Lys Asn Asp Leu
                260                 265                 270

Ala Ala Ile Glu Asn Tyr Leu Asn Lys Thr Ser Trp Asn His Ser Val
                275                 280                 285

Phe Asp Val Pro Leu His Tyr Asn Leu Tyr Asn Ala Ser Asn Ser Gly
                290                 295                 300

Gly Tyr Arg Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
                340                 345                 350

Tyr Ala Leu Ile Leu Thr Arg Glu Gln Gly Tyr Pro Ser Val Phe Tyr
                355                 360                 365

Gly Asp Tyr Tyr Gly Ile Pro Thr His Gly Val Pro Ser Met Lys Ser
                370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
                405                 410                 415

Gly Asp Ser Ser His Pro Asn Ser Gly Leu Ala Thr Ile Met Ser Asp
                420                 425                 430

Gly Pro Gly Gly Asn Lys Trp Met Tyr Val Gly Lys His Lys Ala Gly
                435                 440                 445

Gln Val Trp Arg Asp Ile Thr Gly Asn Arg Ser Gly Thr Val Thr Ile
                450                 455                 460

Asn Ala Asp Gly Trp Gly Asn Phe Thr Val Asn Gly Gly Ala Val Ser
465                 470                 475                 480

Val Trp Val Lys Gln
                485

<210> SEQ ID NO 18
<211> LENGTH: 485
<212> TYPE: PRT
<213> ORGANISM: Bacillus SP.7-7

<400> SEQUENCE: 18

His His Asn Gly Thr Asn Gly Thr Met Met Gln Tyr Phe Glu Trp Tyr
1               5                   10                  15
```

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Gly Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Cys Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly

```
            435                 440                 445
Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Asn
                485

<210> SEQ ID NO 19
<211> LENGTH: 485
<212> TYPE: PRT
<213> ORGANISM: Bacillus sp.707

<400> SEQUENCE: 19

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320
```

```
His Pro Ser His Ala Val Thr Phe Val Asp Asn His Asp Ser Gln Pro
            325                 330                 335
Glu Glu Ala Leu Glu Ser Phe Val Glu Glu Trp Phe Lys Pro Leu Ala
            340                 345             350
Tyr Ala Leu Thr Leu Thr Arg Glu Gln Gly Tyr Pro Ser Val Phe Tyr
            355                 360             365
Gly Asp Tyr Tyr Gly Ile Pro Thr His Gly Val Pro Ala Met Arg Ser
    370                 375                 380
Lys Ile Asp Pro Ile Leu Glu Ala Arg Gln Lys Tyr Ala Tyr Gly Lys
385                 390                 395                 400
Gln Asn Asp Tyr Leu Asp His His Asn Ile Ile Gly Trp Thr Arg Glu
                405                 410                 415
Gly Asn Thr Ala His Pro Asn Ser Gly Leu Ala Thr Ile Met Ser Asp
            420                 425                 430
Gly Ala Gly Gly Ser Lys Trp Met Phe Val Gly Arg Asn Lys Ala Gly
            435                 440                 445
Gln Val Trp Ser Asp Ile Thr Gly Asn Arg Thr Gly Thr Val Thr Ile
    450                 455                 460
Asn Ala Asp Gly Trp Gly Asn Phe Ser Val Asn Gly Gly Ser Val Ser
465                 470                 475                 480
Ile Trp Val Asn Lys
            485
```

ALPHA-AMYLASE VARIANTS WITH ALTERED PROPERTIES

CROSS-REFERENCE TO RELATED APPLICATIONS

This application is a continuation of U.S. application Ser. No. 11/571,708 (now abandoned) filed on Nov. 26, 2007 which is a 35 U.S.C. 371 national application of PCT/DK2005/000469 filed Jul. 5, 2005, which claims priority or the benefit under 35 U.S.C. 119 of Danish application nos. 2004 01325 and 2004 01059 filed Sep. 2, 2004 and Jul. 5, 2004 and U.S. provisional application nos. 60/609,065 (now expired) and 60/585,763 (now expired) filed Sep. 10, 2004 and Jul. 6, 2004, the contents of which are fully incorporated herein by reference.

FIELD OF THE INVENTION

The present invention relates to variants (mutants) of parent Termamyl-like alpha-amylases, which variant has alpha-amylase activity and exhibits an alteration in at least one of the following properties relative to said parent alpha-amylase: Substrate specificity, substrate binding, substrate cleavage pattern, thermal stability, pH activity profile, pH stability profile, stability towards oxidation, $Ca^{2+}$ dependency, reduced and increased pI and improved wash performance, specific activity, stability under, e.g., high temperature and/or low/high pH conditions, in particular at low calcium concentrations, and stability in the presence of detergent, e.g. storage stability in the detergents. The variant of the invention are suitable for starch conversion, ethanol production, laundry wash, dish wash, hard surface cleaning, textile desizing, and/or sweetener production.

BACKGROUND OF THE INVENTION

Alpha-Amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides.

The object of the invention is to provide an improved alpha-amylase, in particular suitable for detergent use.

SUMMARY OF THE INVENTION

The object of the present invention is to provide Termamyl-like amylases which variants in comparison to the corresponding parent alpha-amylase, i.e., un-mutated alpha-amylase, has alpha-amylase activity and exhibits an alteration in at least one of the above properties relative to said parent alpha-amylase.

Nomenclature

In the present description and claims, the conventional one-letter and three-letter codes for amino acid residues are used. For ease of reference, alpha-amylase variants of the invention are described by use of the following nomenclature:

Original amino acid(s): position(s): substituted amino acid(s)

According to this nomenclature, for instance the substitution of alanine for asparagine in position 30 is shown as:

Ala30Asn or A30N a deletion of alanine in the same position is shown as:

Ala30* or A30* and insertion of an additional amino acid residue, such as lysine, is shown as:

Ala30AlaLys or A30AK

A deletion of a consecutive stretch of amino acid residues, such as amino acid residues 30-33, is indicated as (30-33)* or Δ(A30-N33).

Where a specific alpha-amylase contains a "deletion" in comparison with other alpha-amylases and an insertion is made in such a position this is indicated as:

*36Asp or *36D for insertion of an aspartic acid in position 36.

Multiple mutations are separated by plus signs, i.e.:

Ala30Asn+Glu34Ser or A30N+E34S representing mutations in positions 30 and 34 substituting alanine and glutamic acid for asparagine and serine, respectively.

When one or more alternative amino acid residues may be inserted in a given position it is indicated as A30N,E or A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of: R,N,D,A,C,Q,E,G,H,I,L,K,M,F,P,S,T,W,Y,V.

Further, "A30X" means any one of the following substitutions:

A30R, A30N, A30D, A30C, A30Q, A30E, A30G, A30H, A30I, A30L, A30K, A30M, A30F, A30P, A30S, A30T, A30W, A30Y, or A30V; or in short: A30R,N,D,C,Q,E,G,H,I,L,K,M,F,P,S,T,W,Y,V.

If the parent enzyme—used for the numbering—already has the amino acid residue in question suggested for substitution in that position the following nomenclature is used:

"X30N" or "X30N,V" in the case where for instance one of N or V is present in the wildtype.

Thus, it means that other corresponding parent enzymes are substituted to an "Asn" or "Val" in position 30.

Characteristics of Amino Acid Residues

Charged Amino Acids:

Asp, Glu, Arg, Lys, H is

Negatively Charged Amino Acids (with the Most Negative Residue First):

Asp, Glu

Positively Charged Amino Acids (with the Most Positive Residue First):

Arg, Lys, H is

Neutral Amino Acids:

Gly, Ala, Val, Leu, Ile, Phe, Tyr, Trp, Met, Cys, Asn, Gln, Ser, Thr, Pro

Hydrophobic Amino Acid Residues (with the Most Hydrophobic Residue Listed Last):

Gly, Ala, Val, Pro, Met, Leu, Ile, Tyr, Phe, Trp,

Hydrophilic Amino Acids (with the Most Hydrophilic Residue Listed Last):

Thr, Ser, Cys, Gln, Asn

BRIEF DESCRIPTION OF THE DRAWINGS

FIG. 1 is an alignment of the amino acid sequences of thirteen parent Termamyl-like alpha-amylases.

DETAILED DESCRIPTION OF THE INVENTION

The object of the present invention is to provide polypeptides, such as enzymes, in particular alpha-amylases, with an alteration in at least one of the following properties relative to said parent polypeptide: substrate specificity, substrate binding, substrate cleavage pattern, thermal stability, pH/activity profile, stability towards oxidation, $Ca^{2+}$ dependency, and specific activity, in particular in laundry and dish-wash applications. The properties will be defined further below.

Polypeptide

Polypeptides according to the invention include proteins with biological activity, antimicrobial activity, and enzymatic activity.

Contemplated enzyme activities include proteases, amylases, CGTases, mannanases, maltogenic amylases, glucoamylases, carbohydrases, transferases, lyases, oxidoreductases, lipases.

In one preferred embodiment the enzyme is an alpha-amylase, in particular a *Bacillus* or *Aspergillus* alpha-amylase. In a preferred embodiment the *Bacillus* alpha-amylase is a Termamyl-like amylases.

Polypeptides with biological activity include, EPO, TPO, growth hormones, regulatory peptides, blood coagulation factores, antibodies etc.

The Tertiary Structure of SP722 and Modelling the Tertiary Structures of Another Termamyl-Like Alpha-Amylase.

Mutants of alpha-amylases of the present invention have been found based on the tertiary structure of SP722 shown in APPENDIX 1 of WO 01/66712. Mutants of other polypeptides may be found based on other tertiary structures.

A model of another alkaline Termamyl-like amylase, AA560 has been build based on the SP722 tertiary structure disclosed in APPENDIX 1 of WO 01/66712. The AA560 alpha-amylase is about 87% identical to the template amylase (SP722) and the alignment contains no insertion or deletions.

The findings of the present invention may be applied on Termamyl-like amylases being at least 60% identical, preferably at least 70% identical, more preferably 80% identical, even more preferably 85% identical, even more preferably 90% identical, even more 95% identical, even more 97% identical, even more 99% identical to the Termamyl-like alpha-amylase shown in SEQ ID NO: 12. In a preferably the findings may be used on alkaline Termamyl-like alpha-amylases, especially alkaline alpha-amylases of the same length, without additional amino residues or gaps in an aligned primary structure in comparison to SP722 (SEQ ID NO: 4 shown as number 7 in the alignment in FIG. 1). Especially, the finding may be used on the following alkaline Termamyl-like alpha-amylases: SP690 (SEQ ID NO: 2), SP722 (SEQ ID NO: 4), AA560 (SEQ ID NO: 12), #707 alpha-amylase (SEQ ID NO: 13), the KSM AP 1378 alpha-amylase is disclosed in WO 97/00324, the #SP7-7 alpha-amylase is disclosed in WO 02/10356, or fragment or truncated forms thereof. The latter mentioned alkaline alpha-amylases have very similar tertiary crystal structure around the above-mentioned interactions zones, and have the same primary structure length 485 amino acids.

Contrary hereto, for instance, Termamyl (shown as sequence number 1 in the alignment in FIG. 1) lacks two amino acid residues (positions 1 and 2); has gaps in positions 174 and 181-182; and has three additional amino acid residues in positions 378-381 when aligned with SP722.

BAN (shown as sequence number 4 in the alignment in FIG. 1) lacks five amino acid residues (positions 1-4 and 488); has gaps in positions 174 and 181-182; and has three additional amino acid residues in positions 378-381 if aligned with SP722.

BSG (shown as sequence number 3 in the alignment in FIG. 1) lacks one amino acid residues (position 1); and has 31 additional amino acid residues in positions 489-519 if aligned with SP722. KSM-K36 and KSM-K38 (EP 1,022,334-A) lack five amino acid residues (positions 1 and 2) and has gaps in positions 174 and 181-182 when aligned with SP722.

AA180, AA20 and Amrk385 (Danish patent application no. PA 2000 00347 or PCT/DK01/00133) have one additional amino acid in position 261 when aligned with SP722.

Below it is described how to model a Termamyl-like alpha-amylase from another alpha-amylase. This method can be exprepolated to other polypetides as for instance the above-mentioned.

Modelling of Termamyl-Like Alpha-Amylases

WO 96/23874 provides the tertiary structure (3D Structure), X-ray crystal structural data for a Termamyl-like alpha-amylase, which consists of the 300 N-terminal amino acid residues of the *B. amyloliquefaciens* alpha-amylase (BAN™) and amino acids 301-483 of the C-terminal end of the *B. licheniformis* alpha-amylase (SEQ ID NO: 8). WO 96/23874 further describes methodology for designing (modelling), on the basis of an analysis of the structure of a parent Termamyl-like alpha-amylase, variants of the parent Termamyl-like alpha-amylase which exhibit altered properties relative to the parent.

Other Termamyl-like structures may be modelled in accordance with WO 96/23874, which is hereby incorporated by reference.

In connection with obtaining variant of the present invention the AA560 tertiary structure was designed (modelled) based on the tertiary structure of SP722 (disclosed in APPENDIX 1) as described in Example 1. The structure of other Termamyl-like alpha-amylases (e.g., those disclosed herein) may be built analogously.

Termamyl-Like Alpha-Amylases

A number of alpha-amylases produced by *Bacillus* spp. are highly homologous (identical) on the amino acid level.

The identity of a number of *Bacillus* alpha-amylases can be found in the below Table 1 (ClustalW):

TABLE 1

| | BLA | BAN | AMY1048 | BSG | AA560 | sp.707 | sp.7-7 | AMRK385 | SP690 | M-AP1378 | SP722 | AAI10 | K38 |
|---|---|---|---|---|---|---|---|---|---|---|---|---|---|
| BLA | 100.0 | 80.8 | 65.2 | 65.4 | 68.1 | 67.9 | 67.1 | 70.6 | 68.7 | 68.9 | 70.2 | 70.2 | 62.5 |
| BAN | 80.6 | 100.0 | 64.9 | 65.1 | 66.3 | 66.3 | 65.7 | 67.6 | 66.5 | 66.5 | 68.0 | 68.2 | 59.5 |
| AMY1048 | 53.8 | 53.6 | 100.0 | 75.6 | 54.6 | 54.6 | 55.0 | 57.0 | 56.1 | 55.8 | 55.6 | 56.5 | 48.1 |
| BSG | 61.4 | 61.2 | 86.0 | 100.0 | 62.3 | 62.5 | 63.1 | 64.1 | 63.7 | 63.7 | 63.1 | 65.6 | 55.2 |
| AA560 | 67.8 | 66.2 | 66.0 | 66.2 | 100.0 | 95.5 | 94.6 | 89.7 | 87.0 | 86.0 | 86.8 | 78.6 | 63.7 |
| sp,707 | 67.6 | 66.2 | 66.0 | 66.4 | 95.5 | 100.0 | 92.8 | 90.5 | 87.6 | 86.4 | 86.2 | 79.8 | 63.5 |
| Sp,7-7 | 66.8 | 65.6 | 66.4 | 67.0 | 94.6 | 92.8 | 100.0 | 89.1 | 88.5 | 87.2 | 87.0 | 79.2 | 63.7 |
| AMRK385 | 70.2 | 67.3 | 68.7 | 67.9 | 89.5 | 90.3 | 88.9 | 100.0 | 89.3 | 88.9 | 87.5 | 81.9 | 65.4 |
| SP690 | 68.5 | 66.4 | 67.8 | 67.6 | 87.0 | 87.6 | 88.5 | 89.5 | 100.0 | 95.1 | 87.2 | 81.2 | 65.6 |
| KSM-AP1378 | 68.7 | 66.4 | 67.4 | 67.6 | 86.0 | 86.4 | 87.2 | 89.1 | 95.1 | 100.0 | 86.6 | 80.6 | 66.2 |

TABLE 1-continued

| | BLA | BAN | AMY1048 | BSG | AA560 | sp.707 | sp.7-7 | AMRK385 | SP690 | M-AP1378 | SP722 | AAI10 | K38 |
|---|---|---|---|---|---|---|---|---|---|---|---|---|---|
| SP722 | 69.9 | 67.8 | 67.2 | 67.0 | 86.8 | 86.2 | 87.0 | 87.6 | 87.2 | 86.6 | 100.0 | 80.6 | 66.0 |
| AAI10 | 69.9 | 68.0 | 68.3 | 69.7 | 78.6 | 79.8 | 79.2 | 82.1 | 81.2 | 80.6 | 80.6 | 100.0 | 68.5 |
| K38 | 62.9 | 60.0 | 58.8 | 59.2 | 64.4 | 64.2 | 64.4 | 66.3 | 66.3 | 66.9 | 66.7 | 69.2 | 100.0 |

For instance, the *B. licheniformis* alpha-amylase comprising the amino acid sequence shown in SEQ ID NO: 8 (commercially available as Termamyl™) has been found to be about 81% homologous with the *B. amyloliquefaciens* alpha-amylase comprising the amino acid sequence shown in SEQ ID NO: 10 and about 65% homologous with the *B. stearothermophilus* alpha-amylase comprising the amino acid sequence shown in SEQ ID NO: 6. Further homologous alpha-amylases include SP690 and SP722 disclosed in WO 95/26397 and further depicted in SEQ ID NO: 2 and SEQ ID NO: 4, respectively, herein. Other amylases are the AA560 alpha-amylase derived from *Bacillus* sp. and shown in SEQ ID NO: 12, and the #707 alpha-amylase derived from *Bacillus* sp. described by Tsukamoto et al., *Biochemical and Biophysical Research Communications,* 151 (1988), pp. 25-31.

The KSM AP1378 alpha-amylase is disclosed in WO 97/00324 (from KAO Corporation). Also the K38 and K38 alpha-amylases disclosed in EP 1,022,334 are contemplated according to the invention.

Other alpha-amylases are shown in SEQ ID NOS: 13, 14, 15, 16, 17, and 18.

Still further homologous alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like alpha-amylases are comprised in the products sold under the following tradenames: Optitherm™ and Takatherm™ (available from Solvay); Maxamyl™ (available from Gist-brocades/Genencor), Spezym AA™ and Spezyme Delta AA™ (available from Genencor), and Keistase™ (available from Daiwa), Purastar™ ST 5000E, PURASTRA™ HPAM L (from Genencor Int.).

Because of the substantial homology found between these alpha-amylases, they are considered to belong to the same class of alpha-amylases, namely the class of "Termamyl-like alpha-amylases".

Accordingly, in the present context, the term "Termamyl-like alpha-amylase" is intended to indicate an alpha-amylase, which, at the amino acid level, exhibits a substantial identity to Termamyl™, i.e., the *B. licheniformis* alpha-amylase having the amino acid sequence shown in SEQ ID NO: 8 herein.

In other words, all the following alpha-amylases, which has the amino acid sequences shown in SEQ ID NOS: 2, 4, 6, 8, 10, 12, 13, 14, 15, 16, 17, and 18 herein are considered to be "Termamyl-like alpha-amylase". Other Termamyl-like alpha-amylases are alpha-amylases i) which displays at least 60%, such as at least 70%, e.g., at least 75%, or at least 80%, at least 85%, at least 90%, at least 95%, at least 97%, at least 99% homology with at least one of said amino acid sequences shown in SEQ ID NOS: 2, 4, 6, 8, 10, 12, 13, 14, 15, 16, 17 and 18 and/or ii) is encoded by a DNA sequence which hybridizes to the DNA sequences encoding the above-specified alpha-amylases which are apparent from SEQ ID NOS: 1, 3, 5, 7, 9, 11 and of the present specification (which encoding sequences encode the amino acid sequences shown in SEQ ID NOS: 2, 4, 6, 8, 10 and 12 herein, respectively)

Also Termamyl amylases consisting of 1) a catalytic domain with high homology to Termamyl and 2) of a carbohydrate binding domain (CBM) should be understood as included in this application. The Binding domain may be located in either N-terminal relative to the sequence of the catalytic domain or C-terminal relative to the catalytic domain, there might be more than one CBM located either N- or C-terminal or both. The amylases with CBM might come from natural sources or may be the results of genetic engineering fusing the gene coding an amylase with a gene coding a CBM.

Homology (Identity)

The homology may be determined as the degree of identity between the two sequences indicating a derivation of the first sequence from the second. The homology may suitably be determined by means of computer programs known in the art such as GAP provided in the GCG program package (described above). Thus, Gap GCGv8 may be used with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, (1970), J. Mol. Biol. 48, p. 443-453, to make alignments and to calculate the identity.

A structural alignment between Termamyl (SEQ ID NO: 8) and, e.g., another alpha-amylase may be used to identify equiva-lent/corresponding positions in other Termamyl-like alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149-155) and reverse threading (Huber, T; Torda, A E, PROTEIN SCIENCE Vol. 7, No. 1 pp. 142-149 (1998).

Hybridisation

The oligonucleotide probe used in the characterisation of the polypeptide, such as the Termamyl-like alpha-amylase in accordance with property ii) above may suitably be prepared on the basis of the full or partial nucleotide or amino acid sequence of the alpha-amylase in question.

Suitable conditions for testing hybridisation involve presoaking in 5×SSC and prehybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridisation in the same solution supplemented with 100 mM ATP for 18 hours at ~40° C., followed by three times washing of the filter in 2×SSC, 0.2% SDS at 40° C. for 30 minutes (low stringency), preferred at 50° C. (medium stringency), more preferably at 65° C. (high stringency), even more preferably at ~75° C. (very high stringency). More details about the hybridisation method can be found in Sambrook et al., Molecular_Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

Parent Termamyl-Like Alpha-Amylases

According to the invention all Termamy-like alpha-amylases, as defined above, may be used as the parent (i.e., backbone) alpha-amylase. In a preferred embodiment of the invention the parent alpha-amylase is derived from B. licheniformis, e.g., one of those referred to above, such as the B. licheniformis alpha-amylase having the amino acid sequence shown in SEQ ID NO: 10.

In a preferred embodiment the parent Termamyl-like alpha amylase is SP722 or BSG or AA560 including any of SP722+ R181*+G182*, SP722+D183*+G184*; SP722+D183*+ G184*+N195F; SP722+D183*+G184*+M202L; SP722+ D183*+G184*+N195F+M202L; SP722+D183*+G184*+ R181Q; SP722+D183*+G184*+R118K+N195F+R320K+ R458K; BSG+I181*+G182*; BSG+I181*+G182*+N193F; BSG+I181*+G182*+M200L; BSG+I181*+G182*+ N193F+M200L; AA560+D183*+G184*; AA560+D183*+ G184*+N195F; AA560+D183*+G184*+M202L; AA560+ D183*+G184*+N195F+M202L; AA560+D183*+G184*+ R118K+N195F+R320K+R458K. "BSG+I181*+G182*+ N193F" means the B. stearothermophilus alpha-amylase has been mutated as follows: deletions in positions I181 and G182 and a substitution from Asn (N) to Phe (F) in position 193.

Parent Hybrid Termamyl-Like Alpha-Amylases

The parent alpha-amylase (i.e., backbone alpha-amylase) may also be a hybrid alpha-amylase, i.e., an alpha-amylase, which comprises a combination of partial amino acid sequences derived from at least one alpha-amylase.

The parent hybrid alpha-amylase may be one, which on the basis of amino acid homology (identity) and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives, may be any of those specific Termamyl-like alpha-amylase referred to herein.

For instance, the parent alpha-amylase may comprise a C-terminal part of an alpha-amylase derived from a strain of B. licheniformis, and a N-terminal part of an alpha-amylase derived from a strain of B. amyloliquefaciens or from a strain of B. stearothermophilus. For instance, the parent α-amylase may comprise at least 430 amino acid residues of the C-terminal part of the B. licheniformis alpha-amylase, and may, e.g., comprise a) an amino acid segment corresponding to the 37 N-terminal amino acid residues of the B. amyloliquefaciens alpha-amylase having the amino acid sequence shown in SEQ ID NO: 10 and an amino acid segment corresponding to the 445 C-terminal amino acid residues of the B. licheniformis alpha-amylase having the amino acid sequence shown in SEQ ID NO: 8, or a hybrid Termamyl-like alpha-amylase being identical to the Termamyl sequence, i.e., the Bacillus licheniformis alpha-amylase shown in SEQ ID NO: 8, except that the N-terminal 35 amino acid residues (of the mature protein) has been replaced by the N-terminal 33 residues of BAN (mature protein), i.e., the Bacillus amyloliquefaciens alpha-amylase shown in SEQ ID NO: 10; or b) an amino acid segment corresponding to the 68 N-terminal amino acid residues of the B. stearothermophilus α-amylase having the amino acid sequence shown in SEQ ID NO: 6 and an amino acid segment corresponding to the 415 C-terminal amino acid residues of the B. licheniformis alpha-amylase having the amino acid sequence shown in SEQ ID NO: 8.

Another suitable parent hybrid alpha-amylase is the one previously described in WO 96/23874 (from Novo Nordisk) constituting the N-terminus of BAN, Bacillus amyloliquefaciens alpha-amylase (amino acids 1-300 of the mature protein) and the C-terminus from Termamyl (amino acids 301-483 of the mature protein).

Yet another suitable parent hybrid alpha-amylase consist of the sequence of SEQ ID NOS: 2, 4, 6, 8, 10, 12, 13, 14, 15, 16, 17, or 18, and the last 99 amino acids of SEQ ID NO:13 (AMY1048)

In a preferred embodiment of the invention the parent Termamyl-like alpha-amylase is a hybrid alpha-amylase of SEQ ID NO: 8 and SEQ ID NO: 10. Specifically, the parent hybrid Termamyl-like alpha-amylase may be a hybrid alpha-amylase comprising the 445 C-terminal amino acid residues of the B. licheniformis alpha-amylase shown in SEQ ID NO: 8 and the 33 N-terminal amino acid residues of the alpha-amylase derived from B. amyloliquefaciens shown in SEQ ID NO: 10, which may suitably further have the following mutations: H156Y+A181T+N190F+A209V+Q264S (using the numbering in SEQ ID NO: 8). The latter mentioned hybrid is used in the examples below and is referred to as LE174.

Other specifically contemplated parent alpha-amylase include LE174 with fewer mutations, i.e., the right above mentioned hybrid having the following mutations: A181T+ N190F+A209V+Q264S; N190F+A209V+Q264S; A209V+ Q264S; Q264S; H156Y+N190F+A209V+Q264S; H156Y+ A209V+Q264S; H156Y+Q264S; H156Y+A181T+A209V+ Q264S; H156Y+A181T+Q264S; H156Y+Q264S; H156Y+ A181T+N190F+Q264S; H156Y+A181T+N190F; H156Y+ A181T+N190F+A209V. These hybrids are also considered to be part of the invention.

In a preferred embodiment the parent Termamyl-like alpha amylase is LE174 including any of LE174+G48A+T49I+ G107A+I201F; LE174+M197L; or LE174+G48A+T49I+ G107A+M197L+I201F.

Other parent alpha-amylases contemplated include LE429, which is LE174 with an additional substitution in I201F. According to the invention LE335 is the alpha-amylase, which in comparison to LE429 has additional substitutions in T49I+G107A; LE399 is LE335+G48A, i.e., LE174, with G48A+T49I+G107A+I201F.

Construction of Variants of the Invention

The construction of the variant of interest may be accomplished by cultivating a microorganism comprising a DNA sequence encoding the variant under conditions which are conducive for producing the variant. The variant may then subsequently be recovered from the resulting culture broth. This is described in detail further below.

Altered Properties

The following discusses the relationship between mutations, which are present in variants of the invention, and desirable alterations in properties (relative to those of a parent Termamyl-like alpha-amylase), which may result therefrom.

As mentioned above the invention relates to Termamyl-like alpha-amylases with altered properties, in particular at high temperatures and/or at low pH, in particular at low calcium concentrations.

In the context of the present invention "high temperature" means temperatures from 70-120° C., preferably 80-100° C., especially 85-95° C.

In the context of the present invention the term "low pH" means from a pH in the range from 4-6, preferably 4.2-5.5, especially 4.5-5.

In the context of the present invention the term "high pH" means from a pH in the range from 8-11, especially 8.5-10.6.

In the context of the present invention the term "low calcium concentration" means free calcium levels lower than 60 ppm, preferably 40 ppm, more preferably 25 ppm, especially 5 ppm calcium.

Parent Termamyl-like alpha-amylase specifically contemplated in connection with going through the specifically contemplated altered properties are the above mentioned parent Termamyl-like alpha-amylase and parent hydrid Termamyl-like alpha-amylases. The SP722 alpha-amylase is used as the starting point, but corresponding positions in, e.g., the Termamyl, BSG, BAN, AA560, SP690, AA180, KSM AP1378, SP7-7 and #707, K38, and K36 should be understood as disclosed too.

Design of Improved Oxidation Stable Amylase Variants:

M197 in SEQ ID NO: 8 or the equivalent M202 in SEQ ID NO: 12 has been shown to increase the stability in the presence of bleaching agents like e.g. perborate etc. in detergents. Also mutation of M15 in SEQ ID NO: 8 has shown some effect but for SEQ ID NO: 2, 4, 6, 10, and 12 and other amylases which do not have a corresponding methionine at position equivalent to M15, other residues, in particular other Methionines, have been found to increase the stability beyond what is observed for M202. These include but are not limited to M9, M10, M105, M116 (not present in SP690, SP722, AMRK385) M202, M208, M261, M309, M323 (only in AA560, SP722), M382, M410 (SP.7-7), M430, M440, in SEQ ID NO: 12, 17, and 18, whereas in SEQ ID NO: 16 (AAI-10) the most interesting positions are: M10, M105, M202, M208, M246, M286, M309, M430, M440, M454 and whereas in SEQ ID NO: 14(Amrk385) the most interesting positions are: M9, M10, M105, M202, M208, M262, M310, M383, M431, M441, and whereas in SEQ ID NO: 15 (K38) the most interesting positions are: M7, M8, M103, M107, M277, M281, M304, M318, M380, M425, M435. The most preferred substitutions are: M9L,I, M10L, M105L,I,F, M116N,D,L,I,F,W,R,K, M202L,I,T,V, M208F,Y, L,I, M261L,I, M309L,I, M323L,I,S,T,A,Q,E,N,D, M382L,I,Y,F, K, M410L,I,V, M430L,I, M440L,I,F,Y.

As stated above M202 has been shown to be important for the stability in the presence of bleaching agents. However mutating M202 to substitutions preferred for stability, reduces the activity of the amylase. To re-activate the amylase, substitutions along the putative substrate binding cleft has shown to be beneficial for the activity. These include among others: T193, K269, N270, L272, Y295, N296, N299, S303, Y304, Q311, N314, G315, Q319, and A339. The preferred mutations being: T193S,N,D,E,Q, K269S,Q, N270F,Y,D, L272I,V,A, Y295F,N,D,Q,E, N296K,Q,E, N299F,Y,Q,T, S303Q,K, Y304F,R,K, Q311N,Q,K,R,T,S,Y,F, N314D,S,T,Q, G315N,S,T, Q319E,K,S,T, A339S,T.

The optimal enzyme for washing application has to fulfill several criteria to work optimally. It should be stable in the detergent matrix prior to usage, it should be stable during wash and it should be highly active during wash. There are several examples reported for optimizing each of these criteria but as oxidation stabile amylases are less active and activated amylases are less stable, it is the scope of this invention to identify the optimal combination of substitutions fulfilling all three demands. The preferred combinations are:

M9L+M202I
M9L+M202I+M323T
M9L+M202I+M323T+M382Y
M202I+Y295F
M202I+A339S
M9L+M202I+Y295F+A339S
M9L+M202I+Y295F
M9L+M202I+A339S
M9L+M202I+Y295F+A339S
M9L+M202I+Y295F+A339S+E345R
M9L+G149A+M202I+Y295F+A339S+E345R
M9L+M202L
M9L+M202L+M323T
M9L+M202L+M323T+M382Y
M202L+Y295F
M202L+A339S
M9L+M202L+Y295F+A339S
M9L+M202L+Y295F
M9L+M202L+A339S
M9L+M202L+Y295F+A339S
M9L+M202L+Y295F+A339S+E345R
M9L+G149A+M202L+Y295F+A339S+E345R
M9L+M202T
M9L+M202T+M323T
M9L+M202T+M323T+M382Y
M202T+Y295F
M202T+A339S
M9L+M202T+Y295F+A339S
M9L+M202T+Y295F
M9L+M202T+A339S
M9L+M202T+Y295F+A339S
M9L+M202T+Y295F+A339S+E345R
M9L+G149A+M202T+Y295F+A339S+E345R
M9L+G149A+M202I+V214T+Y295F+N299Y+M323T+A339S+E345R
M9L+G149A+M202L+V214I+Y295F+M323T+A339S+E345R+M382Y
M9L+G149A+G182T+G186A+M202I+V214I+Y295F+N299Y+M323T+A339S
M9L+G149A+G182T+G186A+M202L+T257I+Y295F+N299Y+M323T+A339S+E345R
M9L+G149A+M202L+V214I+Y295F+N299Y+M323T+A339S+E345R
M9L+G149A+M202I+V214I+Y295F+M323T+A339S+E345R+M382Y
M9L+G149A+G182T+G186A+M202L+V214I+Y295F+N299Y+M323T+A339S
M9L+G149A+G182T+G186A+M202I+T257I+Y295F+N299Y+M323T+A339S+E345R
M9L+G149A+M202I+V214T+Y295F+N299Y+M323T+A339S+E345R+N471E
M9L+G149A+M202L+V214I+Y295F+M323T+A339S+E345R+M382Y+N471E
M9L+G149A+G182T+G186A+M202I+V214I+Y295F+N299Y+M323T+A339S+N471E
M9L+G149A+G182T+G186A+M202L+T257I+Y295F+N299Y+M323T+A339S+E345R+N471E

In the first aspect a variant of a parent Termamyl-like alpha-amylase, comprising an alteration at one or more positions selected from the group of:

26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, wherein
- (a) the alteration(s) are independently
  - (i) an insertion of an amino acid downstream of the amino acid which occupies the position,
  - (ii) a deletion of the amino acid which occupies the position, or
  - (iii) a substitution of the amino acid which occupies the position with a different amino acid,
- (b) the variant has alpha-amylase activity, and
- (c) each position corresponds to a position of the amino acid sequence of the parent alpha-amylase having the amino acid sequence of the parent Termamyl-like alpha-amylase having the amino acid sequence of AA560 shown in SEQ ID NO: 12.

In a preferred embodiment the variant of the invention (using SEQ ID NO: 12 for the numbering) has one or more of the following mutations/substitutions:

R26S, D30N, N33D, R82H, K37T, N106D, K118Q, N128Y, G133E,A, G149A,N, N150H,Q, Y160F, Y178F, G182T, G186A, T193S,N,D,E,Q, Y203L, V214I,T, D231N, G256K, T257I, G258D, K269S,Q, N270F,Y,D, L272I,V,A, N283D, Y295F,N,D,Q,E, N296K,Q,E, Y298F,H, N299F,Y, Q,T, S303Q,K, Y304F,R,K, G305D, Q311N,Q,K,R,T,S,Y,F, N314D,S,T,Q, G315N,S,T, V318L, Q319E,K,S,T, A339S,T, E345N,R, Q361E, G378K, K383R, T419N, H421Y, N437H, F441L, R444E,Y, N445Q, K446R, A447Y, V450T, T461P, N471E, W482Y, N484Q.

Preferred double, triple and multi-mutations—using SEQ ID NO: 12 as the basis for the numbering—include:

M9L+M202I,
M9L+M202I+M323T,
M9L+M202I+323T+M382Y,
M9L+M202I+Y295F+A339S,
M9L+M202I+Y295F,
M9L+M202I+A339S,
M9L+M202I+Y295F+A339S,
M9L+M202I+Y295F+A339S+E345R,
M9L+G149A+M202I+Y295F+A339S+E345R,
M9L+M202L,
M9L+M202L+M323T,
M9L+M202L+M232T+M382Y,
M9L+M202L+Y295F+A339S,
M9L+M202L+Y295F,
M9L+M202L+A339S,
M9L+M202L+Y295F+A339S,
M9L+M202L+Y295F+A339S, E345R,
M9L+G149A+M202L+Y295F+A339S+E345R,
M9L+M202T,
M9L+M202T+M323T,
M9L+M202T+M323T+M382Y,
M9L+M202T+Y295F+A339S,
M9L+M202T+Y295F,
M9L+M202T+A339S,
M9L+M202T+Y295F+A339S,
M9L+M202T+Y295F+A339S+E345R,
M9L+G149A+M202T+Y295F+A339S+E345R,
M9L+G149A+M202I+V214T+Y295F+N299Y+M323T+A339S+E345R,
M9L+G149A+M202L+V214I+Y295F+M323T+A339S+E345R+M382Y,
M9L+G149A+G182T+G186A+M202I+V214I+Y295F+N299Y+M323T+A339S,
M9L+G149A+G182T+G186A+M202L+T257I+Y295F+N299Y+M323T+A339S+E345R,
M9L+G149A+M202L+V214T+Y295F+N299Y+M323T+A339S+E345R,
M9L+G149A+M202I+V214I+Y295F+M323T+A339S+E345R+M382Y,
M9L+G149A+G182T+G186A+M202L+V214I+Y295F+N299Y+M323T+A339S,
M9L+G149A+G182T+G186A+M202I+T257I+Y295F+N299Y+M323T+A339S+E345R,
M9L+G149A+M202I+V214T+Y295F+N299Y+M323T+A339S+E345R+N471E,
M9L+G149A+M202L+V214I+Y295F+M323T+A339S+E345R+M382Y+N471E,
M9L+G149A+G182T+G186A+M202I+V214I+Y295F+N299Y+M323T+A339S+N471E,
M9L+G149A+G182T+G186A+M202L+T257I+Y295F+N299Y+M323T+A339S+E345R+N471E,
M202L+M105F+M208F,
G133E+M202L+Q361E,
G133E+M202L+R444E,
M202L+Y295F,
M202L+A339S,
M202L+M323T,
M202L+M323T+M309L,
M202L+M323T+M430I,
M202L+V214T+R444Y,
M202L+N283D+Q361E,
M202L+M382Y+K383R,
M202L+K446R+N484Q,
M202I+Y295F,
M202I+A339S,
M202I+M105F+M208F,
G133E+M202I+Q361E,
G133E+M202I+R444E,
M202I+M202I+M323T,
M202I+M202I+M323T+M309L,
M202I+M323T+M430I,
M202I+V214T+R444Y,
M202I+N283D+Q361E,
M202I+M382Y+K383R,
M202I+K446R+N484Q,
M202V+M105F+M208F,
G133E+M202V+Q361E,
G133E+M202V+R444E,
M202V+M323T,
M202V+M323T+M309L,
M202V+M323T+M430I,
M202V+M323T+M9L,
M202V+V214T+R444Y,
M202V+N283D+Q361E,
M202V+M382Y+K383R,
M202V+K446R+N484Q,
M202T+M105F+M208F,
G133E+M202T+Q361E,
G133E+M202T+R444E,
M202T+Y295F,
M202T+A339S,
M202T+M323T,
M202T+M323T+M309L,
M202T+M323T+M430I,
M202T+M323T+M9L,
M202T+V214T+R444Y,

M202T+N283D+Q361E,
M202T+A339S,
M202T+Y295F
M202T+N299F,Y,
M202T+M382Y+K383R,
M202T+K446R+N484Q

Stability

In the context of the present invention, mutations (including amino acid substitutions and deletion) of importance with respect to achieving altered stability, in particular improved stability (i.e., higher or lower), at especially high temperatures (i.e., 70-120° C.) and/or extreme pH (i.e. low or high pH, i.e, pH 4-6 or pH 8-11, respectively), in particular at free (i.e., unbound, therefore in solution) calcium concentrations below 60 ppm, include any of the mutations listed in the "Altered Properties" section. The stability may be determined as described in the "Materials & Methods" section below.

$Ca^{2+}$ Stability

Altered $Ca^{2+}$ stability means the stability of the enzyme under $Ca^{2+}$ depletion has been improved, i.e., higher or lower stability. In the context of the present invention, mutations (including amino acid substitutions and deletions) of importance with respect to achieving altered $Ca^{2+}$ stability, in particular improved $Ca^{2+}$ stability, i.e., higher or lower stability, at especially high pH (i.e., pH 8-10.5) include any of the mutations listed in the "Altered properties" section.

Specific Activity

In a further aspect of the present invention, important mutations (including amino acid substitutions and deletions) with respect to obtaining variants exhibiting altered specific activity, in particular increased or decreased specific activity, especially at temperatures from 10-60° C., preferably 20-50° C., especially 30-40° C., include any of the mutations listed in the "Altered properties" section. The specific activity may be determined as described in the "Material & Methods" section below.

Oxidation Stability

Variants of the invention may have altered oxidation stability, in particular higher oxidation stability, in comparison to the parent alpha-amylase. Increased oxidation stability is advantageous in, e.g., detergent compositions and descresed oxidation stability may be advantageous in composition for starch liquefaction. Oxidation stability may be determined as described in the "Material & Methods" section below.

Altered pH Profile

Important positions and mutations with respect to obtaining variants with altered pH profile, in particular improved activity at especially high pH (i.e., pH 8-10.5) or low pH (i.e., pH 4-6) include mutations of amino residues located close to the active site residues.

Preferred specific mutations/substitutions are the ones listed above in the section "Altered Properties" for the positions in question. Suitable assays are described in the "Materials & Methods" section below.

Wash Performance

Important positions and mutations with respect to obtaining variants with improved wash performance at especially neutral to high pH, i.e., pH 6-11, preferably pH 8.5-11 include the specific mutations/substitutions listed above in the section "Altered Properties" for the positions in question. The wash performance may be tested as described below in the "Materials & Methods" section.

Methods for Preparing Alpha-Amylase Variants of the Invention

Several methods for introducing mutations into genes are known in the art. After a brief discussion of the cloning of alpha-amylase-encoding DNA sequences, methods for generating mutations at specific sites within the alpha-amylase-encoding sequence will be discussed.

Cloning a DNA Sequence Encoding an Alpha-Amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labeled oligonucleotide probes may be synthesized and used to identify alpha-amylase-encoding clones from a genomic library prepared from the organism in question. Alternatively, a labeled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by S. L. Beaucage and M. H. Caruthers, *Tetrahedron Letters* 22, 1981, pp. 1859-1869 or the method described by Matthes et al., *The EMBO J.* 3, 1984, pp. 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., *Science* 239, 1988, pp. 487-491.

Site-Directed Mutagenesis

Once an alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 disclose the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Alternative methods for providing variants of the invention include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question.

Random Mutagenesis

Random mutagenesis is suitably performed either as localised or region-specific random mutagenesis in at least three parts of the gene translating to the amino acid sequence shown in question, or within the whole gene.

The random mutagenesis of a DNA sequence encoding a parent alpha-amylase may be conveniently performed by use of any method known in the art.

In relation to the above, a further aspect of the present invention relates to a method for generating a variant of a parent alpha-amylase, e.g., wherein the variant exhibits a reduced capability of cleaving an oligo-saccharide substrate close to the branching point, and further exhibits improved substrate specificity and/or improved specific activity relative to the parent, the method:

(a) subjecting a DNA sequence encoding the parent alpha-amylase to random mutagenesis, (b) expressing the mutated DNA sequence obtained in step (a) in a host cell, and (c) screening for host cells expressing an alpha-amylase variant which has an altered property (i.e., thermal stability) relative to the parent alpha-amylase.

Step (a) of the above method of the invention is preferably performed using doped primers. For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one, which induces transitions, transversions, inversions, scrambling, deletions, and/or insertions. Examples of a physical or chemical mutagenizing agent suitable for the present purpose include ultraviolet (UV) ir-radiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties. When the mutagenesis is performed by the use of an oligonucleotide, the oligonucleotide may be doped or spiked with the three non-parent nucleotides during the synthesis of the oligonucleotide at the positions, which are to be changed. The doping or spiking may be done so that codons for unwanted amino acids are avoided. The doped or spiked oligonucleotide can be incorporated into the DNA encoding the alpha-amylase enzyme by any published technique, using e.g., PCR, LCR or any DNA polymerase and ligase as deemed appropriate. Preferably, the doping is carried out using "constant random doping", in which the percentage of wild type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program, which, inter alia, ensures that introduction of stop codons is avoided. When PCR-generated mutagenesis is used, either a chemically treated or non-treated gene encoding a parent alpha-amylase is subjected to PCR under conditions that increase the misincorporation of nucleotides (Deshler 1992; Leung et al., Technique, Vol. 1, 1989, pp. 11-15). A mutator strain of E. coli (Fowler et al., Molec. Gen. Genet., 133, 1974, pp. 179-191), S. cereviseae or any other microbial organism may be used for the random mutagenesis of the DNA encoding the alpha-amylase by, e.g., transforming a plasmid containing the parent glycosylase into the mutator strain, growing the mutator strain with the plasmid and isolating the mutated plasmid from the mutator strain. The mutated plasmid may be subsequently transformed into the expression organism. The DNA sequence to be mutagenized may be conveniently present in a genomic or cDNA library prepared from an organism expressing the parent alpha-amylase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence. In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme. Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium*, *Bacillus thuringiensis*, *Streptomyces lividans* or *Streptomyces murinus*; and gram-negative bacteria such as *E. coli*. The mutated DNA sequence may further comprise a DNA sequence encoding functions permitting expression of the mutated DNA sequence.

Localised Random Mutagenesis

The random mutagenesis may be advantageously localised to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localised, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative Methods of Providing Alpha-Amylase Variants

Alternative methods for providing variants of the invention include gene-shuffling method known in the art including the methods e.g., described in WO 95/22625 (from Affymax Technologies N.V.) and WO 96/00343 (from Novo Nordisk A/S).

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector that may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, poly-adenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* α-amylases mentioned herein comprises a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an ad-vantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are Gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram-negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In a yet further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

INDUSTRIAL APPLICATIONS

The alpha-amylase variants of this invention possess valuable properties allowing for a variety of industrial applications. In particular, enzyme variants of the invention are applicable as a component in washing, dishwashing, and hard surface cleaning detergent compositions.

Variant of the invention with altered properties may be used for starch processes, in particular starch conversion, especially liquefaction of starch (see, e.g., U.S. Pat. No. 3,912,590, EP patent application nos. 252 730 and 63 909, WO 99/19467, and WO 96/28567 all references hereby incorporated by reference). Also contemplated are compositions for starch conversion purposes, which may beside the variant of the invention also comprise a glucoamylase, pullulanase, and other alpha-amylases.

Further, variants of the invention are also particularly useful in the production of sweeteners and ethanol (see, e.g., U.S. Pat. No. 5,231,017 hereby incorporated by reference), such as fuel, drinking and industrial ethanol, from starch or whole grains.

Variants of the invention may also be useful for desizing of textiles, fabrics and garments (see, e.g., WO 95/21247, U.S. Pat. No. 4,643,736, EP 119,920 hereby in corporate by reference), beer making or brewing, in pulp and paper production, and in the production of feed and food.

Starch Conversion

Conventional starch-conversion processes, such as liquefaction and saccharification processes are described, e.g., in U.S. Pat. No. 3,912,590 and EP patent publications Nos. 252,730 and 63,909, hereby incorporated by reference.

In an embodiment the starch conversion process degrading starch to lower molecular weight carbohydrate components such as sugars or fat replacers includes a debranching step.

Starch to Sugar Conversion

In the case of converting starch into a sugar the starch is depolymerized. A such depolymerization process consists of a Pre-treatment step and two or three consecutive process steps, viz. a liquefaction process, a saccharification process and dependent on the desired end product optionally an isomerization process.

Pre-Treatment of Native Starch

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typically industrial process, the starch has to be thinned or "liquefied" so that it can be handled. This reduction in viscosity is today mostly obtained by enzymatic degradation.

Liquefaction

During the liquefaction step, the long chained starch is degraded into branched and linear shorter units (maltodextrins) by an alpha-amylase. The liquefaction process is carried out at 105-110° C. for 5 to 10 minutes followed by 1-2 hours at 95° C. The pH lies between 5.5 and 6.2. In order to ensure optimal enzyme stability under these conditions, 1 mM of calcium is added (40 ppm free calcium ions). After this treatment the liquefied starch will have a "dextrose equivalent" (DE) of 10-15.

Saccharification

After the liquefaction process the maltodextrins are converted into dextrose by addition of a glucoamylase (e.g., AMG) and a debranching enzyme, such as an isoamylase (U.S. Pat. No. 4,335,208) or a pullulanase (e.g., Promozyme™) (U.S. Pat. No. 4,560,651). Before this step the pH is reduced to a value below 4.5, maintaining the high temperature (above 95° C.) to inactivate the liquefying alpha-amylase to reduce the formation of short oligosaccharide called "panose precursors" which cannot be hydrolyzed properly by the debranching enzyme.

The temperature is lowered to 60° C., and glucoamylase and debranching enzyme are added. The saccharification process proceeds for 24-72 hours.

Normally, when denaturing the α-amylase after the liquefaction step about 0.2-0.5% of the saccharification product is the branched trisaccharide $6^2$-alpha-glucosyl maltose (panose) which cannot be degraded by a pullulanase. If active amylase from the liquefaction step is present during saccharification (i.e., no denaturing), this level can be as high as 1-2%, which is highly undesirable as it lowers the saccharification yield significantly.

Isomerization

When the desired final sugar product is, e.g., high fructose syrup the dextrose syrup may be converted into fructose. After the saccharification process the pH is increased to a value in the range of 6-8, preferably pH 7.5, and the calcium is removed by ion exchange. The dextrose syrup is then converted into high fructose syrup using, e.g., an immobilized glucoseisomerase (such as Sweetzyme™ IT).

Ethanol Production

In general alcohol production (ethanol) from whole grain can be separated into 4 main steps Milling
Liquefaction
Saccharification
Fermentation Milling The grain is milled in order to open up the structure and allowing for further processing. Two processes are used wet or dry milling. In dry milling the whole kernel is milled and used in the remaining part of the process. Wet milling gives a very good separation of germ and meal (starch granules and protein) and is with a few exceptions applied at locations where there is a parallel production of syrups.

Liquefaction

In the liquefaction process the starch granules are solubilized by hydrolysis to maltodextrins mostly of a DP higher than 4. The hydrolysis may be carried out by acid treatment or enzymatically by alpha-amylase. Acid hydrolysis is used on a limited basis. The raw material can be milled whole grain or a side stream from starch processing.

Enzymatic liquefaction is typically carried out as a three-step hot slurry process. The slurry is heated to between 60-95° C., preferably 80-85° C., and the enzyme(s) is (are) added. Then the slurry is jet-cooked at between 95-140° C., preferably 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

Saccharification

To produce low molecular sugars $DP_{1-3}$ that can be metabolized by yeast, the maltodextrin from the liquefaction must be further hydrolyzed. The hydrolysis is typically done enzymatically by glucoamylases, alternatively alpha-glucosidases or acid alpha-amylases can be used. A full saccharification step may last up to 72 hours, however, it is common only to do a pre-saccharification of typically 40-90 minutes and then complete saccharification during fermentation (SSF). Saccharification is typically carried out at temperatures from 30-65° C., typically around 60° C., and at pH 4.5.

Fermentation

Yeast typically from *Saccharomyces* spp. is added to the mash and the fermentation is ongoing for 24-96 hours, such as typically 35-60 hours. The temperature is between 26-34° C., typically at about 32° C., and the pH is from pH 3-6, preferably around pH 4-5.

Note that the most widely used process is a simultaneous saccharification and fermentation (SSF) process where there is no holding stage for the saccharification, meaning that yeast and enzyme is added together. When doing SSF it is common to introduce a pre-saccharification step at a temperature above 50° C., just prior to the fermentation.

Distillation

Following the fermentation the mash is distilled to extract the ethanol.

The ethanol obtained according to the process of the invention may be used as, e.g., fuel ethanol; drinking ethanol, i.e., potable neutral spirits; or industrial ethanol.

By-Products

Left over from the fermentation is the grain, which is typically used for animal feed either in liquid form or dried.

Further details on how to carry out liquefaction, saccharification, fermentation, distillation, and recovering of ethanol are well known to the skilled person.

According to the process of the invention the saccharification and fermentation may be carried out simultaneously or separately.

Pulp and Paper Production

The alkaline alpha-amylase of the invention may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase of the invention is especially useful in a process for producing a papermaking pulp from starch-coated printed-paper. The process may be performed as described in WO 95/14807, comprising the following steps:

a) disintegrating the paper to produce a pulp,
b) treating with a starch-degrading enzyme before, during or after step a), and
c) separating ink particles from the pulp after steps a) and b).

The alpha-amylases of the invention may also be very useful in modifying starch where enzymatically modified starch is used in papermaking together with alkaline fillers such as calcium carbonate, kaolin and clays. With the alkaline alpha-amylases of the invention it becomes possible to modify the starch in the presence of the filler thus allowing for a simpler integrated process.

Desizing of Textiles, Fabrics and Garments

An alpha-amylase of the invention may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fiber damage because of the rather aggressive chemicals used. Accordingly, it would be desirable to use the alpha-amylases of the invention as they have an improved performance in alkaline solutions. The alpha-amylases may be used alone or in combination with a cellulase when desizing cellulose-containing fabric or textile.

Desizing and bleaching processes are well known in the art. For instance, such processes are described in WO 95/21247, U.S. Pat. No. 4,643,736, EP 119,920 hereby incorporate by reference.

Commercially available products for desizing include AQUAZYME® and AQUAZYME® ULTRA from Novozymes A/S.

Beer Making

The alpha-amylases of the invention may also be very useful in a beer-making process; the alpha-amylases will typically be added during the mashing process.

Detergent Compositions

The alpha-amylase of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a peroxidase, another amylolytic enzyme, e.g., another alpha-amylase, glucoamylase, maltogenic amylase, CGTase and/or a cellulase, mannanase (such as MANNAWAY™ brand mannase from Novozymes, Denmark), pectinase, pectine lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like pro-teases are trypsin (e.g., of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include ALCALASE® brand protease, SAVINASE® brand protease, PRIMASE® brand protease, DURALASE® brand protease, ESPERASE® brand protease, and KANNASE® brand protease (from Novozymes A/S), MAXATASE® brand protease, MAXACAL brand protease MAXAPEM® brand protease, PROPERASE® brand protease, PURAFECT® brand protease, PURAFECT OXP® brand protease, FN2® brand protease, FN3® brand protease, FN4® brand protease (Genencor International Inc.).

Lipases: Suitable lipases include those of bacterial or fungal origin. Chemically modified or protein engineered mutants are included. Examples of useful lipases include lipases from Humicola (synonym Thermomyces), e.g., from H. lanuginosa (T. lanuginosus) as described in EP 258 068 and EP 305 216 or from H. insolens as described in WO 96/13580, a Pseudomonas lipase, e.g., from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g., from B. subtilis (Dartois et al. (1993), Biochemica et Biophysica Acta, 1131, 253-360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ brand lipase and LIPOLASE ULTRA™ brand lipase (Novozymes A/S).

Amylases: Suitable amylases (alpha and/or beta) include those of bacterial or fungal origin. Chemically modified or protein engineered mutants are included. Amylases include, for example, alpha-amylases obtained from Bacillus, e.g., a special strain of B. licheniformis, described in more detail in GB 1,296,839. Examples of useful alpha-amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available alpha-amylases are DURAMYL™ brand alpha-amylase, LIQUEZYME™ brand alpha-amylase, TERMAMYL™ brand alpha-amylase, NATALASE™ brand alpha-amylase, SUPRAMYL™ brand alpha-amylase, STAINZYME™ brand alpha-amylase, FUNGAMYL™ brand alpha-amylase and BAN™ brand alpha-amylase (Novozymes A/S), RAPIDASE™ brand alpha-amylase, PURASTAR™ brand alpha-amylase and PURASTAR OXAM™ brand alpha-amylase, (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellu-lases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME® brand cellulase and CAREZYME® brand cellulase (Novozymes A/S), CLAZINASE® brand cellulase, and PURADAX HA® brand cellulase (Genencor International Inc.), and KAC-500(B)® brand cellulase (Kao Corporation).

Peroxidases/Oxidases: Suitable peroxidases/oxidases include those of plant, bac-terial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257.

Commercially available peroxidases include GUARDZYME® brand peroxidase (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme pre-parations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, tripho-sphate, phosphonate, carbonate, citrate, nitrilotriacetic acid, ethylenediaminetetraacetic acid, diethylenetri-aminepen-taacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxy-ben-zenesul-fonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.001-100 mg of enzyme protein per liter of wash liquor, preferably 0.005-5 mg of enzyme protein per liter of wash liquor, more preferably 0.01-1 mg of enzyme protein per liter of wash liquor and in particular 0.1-1 mg of enzyme protein per liter of wash liquor.

The enzyme of the invention may additionally be incorporated in the detergent formulations disclosed in WO 97/07202, which is hereby incorporated as reference.

Dishwash Detergent Compositions

The enzyme of the invention may also be used in dish wash detergent compositions, including the following:

1) Powder Automatic Dishwashing Composition

| | |
|---|---:|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

2) Powder Automatic Dishwashing Composition

| | |
|---|---:|
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dehydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10 |

3) Powder Automatic Dishwashing Composition

| | |
|---|---:|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

4) Powder Automatic Dishwashing Composition

| | |
|---|---:|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

5) Powder Automatic Dishwashing Composition

| | |
|---|---:|
| Nonionic surfactant | 1-7% |
| Sodium disilicate | 18-30% |
| Trisodium citrate | 10-24% |
| Sodium carbonate | 12-20% |
| Monopersulphate (2 $KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

6) Powder and Liquid Dishwashing Composition with Cleaning Surfactant System

| | |
|---|---|
| Nonionic surfactant | 0-1.5% |
| Octadecyl dimethylamine N-oxide dehydrate | 0-5% |
| 80:20 wt. C18/C16 blend of octadecyl dimethylamine N-oxide dihydrate and hexadecyldimethyl amine N-oxide dehydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |

7) Non-Aqueous Liquid Automatic Dishwashing Composition

| | |
|---|---|
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

8) Non-Aqueous Liquid Dishwashing Composition

| | |
|---|---|
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

9) Thixotropic Liquid Automatic Dishwashing Composition

| | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

10) Liquid Automatic Dishwashing Composition

| | |
|---|---|
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dehydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

11) Liquid Automatic Dishwashing Composition Containing Protected Bleach Particles

| | |
|---|---|
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

12) Automatic dishwashing compositions as described in 1), 2), 3), 4), 6) and 10), wherein perborate is replaced by percarbonate.

13) Automatic dishwashing compositions as described in 1)-6) which additionally contain a manganese catalyst. The manganese catalyst may, e.g., be one of the compounds described in "Efficient manganese catalysts for low-temperature bleaching", *Nature* 369, 1994, pp. 637-639.

Materials and Methods

Enzymes:

SP722: SEQ ID NO: 4, available from Novozymes, and disclosed in WO 95/26397.

AA560: SEQ ID NO: 12; disclosed in WO 00/60060 and available from Novozymes A/S; disclosed in Danish patent application no. PA 1999 00490; deposited on 25 Jan. 1999 at DSMZ and assigned the DSMZ no. 12649.

AA560 were deposited under the terms of the Budapest Treaty on the International Recognition of the Deposit of Microorganisms for the Purposes of Patent Procedure at Deutshe Sammmlung von Microorganismen und Zellkulturen GmbH (DSMZ), Mascheroder Weg 1b, D-38124 Braunschweig DE.

AX379: Available from Novozymes.

*Bacillus subtilis* SHA273: see WO 95/10603

Plasmids pJE1 contains the gene encoding a variant of SP722 alpha-amylase (SEQ ID NO: 4): viz. deletion of 6 nucleotides corresponding to amino acids D183-G184 in the mature protein. Transcription of the JE1 gene is directed from the amyL promoter. The plasmid further more contains the origin of replication and cat-gene conferring resistance towards chloramphinicol obtained from plasmid pUB110 (Gryczan, T J et al. (1978), J. Bact. 134:318-329).

pDN1528 contains the complete gene encoding Termamyl, amyL, the expression of which is directed by its own promoter. Further, the plasmid contains the origin of replication, ori, from plasmid pUB110 and the cat gene from plasmid pC194 conferring resistance towards chloramphenicol. pDN1528 is shown in FIG. 9 of WO 96/23874.

Methods:
General Molecular Biology Methods:

Unless otherwise mentioned the DNA manipulations and transformations were performed using standard methods of molecular biology (Sambrook et al. (1989); Ausubel et al. (1995); Harwood and Cutting (1990).

Modelbuilinq

Protein structure databases, such as "The Protein Data Bank (PDB) see website at (www.pdb.bnl.gov)" or "The Brookhaven databank at Brookhaven National Laboratory, US" are search for proteins similar to the molecule in question that a model are to be build of. The amino acid sequences are aligned taking structurally conserved regions into consideration and the coordinates are copied from the reference protein to the subject protein. The coordinates for regions with insertions and deletions are assigned either from other proteins having similar amino acid sequence, or by using the random structure generator function found in most 3D software packages, eg. in Homology from Biosym, MSI.

When coordinates have been assigned to all amino acids of the subjective protein and the fragments have been linked together, example by the cormands END REPAIR and SPLICE REPAIR, in the Discover program from Biosym, MSI, the model are to be refined. The energy of the model is minimised first by relaxing the molecule (RELAX command in the Discover program) and second minimised by molecular dynamics.

References can be found in and in the manuals of homology building software, eg. Homology from Biosym, MSI Method for Obtaining the Regions of Interest:

There are three known 3D structures of bacterial α-amylases. Two of B. licheniformis α-amylase, Brookhaven database 1BPL (Machius et al. (1995), J. Mol. Biol. 246, p. 545-559) and 1VJS (Song et al. (1996), Enzymes for Carbohydrate 163 Engineering (Prog. Biotechnol. V 12). These two structures are lacking an important piece of the structure from the so-called B-domain, in the area around the two Calcium ions and one Sodium ion binding sites. There also exist a 3D structure of an alpha-amylase BA2 (WO 96/23874 which is a hybrid between BAN™ (SEQ ID NO. 5) and B. licheniformis alpha-amylase (SEQ ID NO. 4) published, which contains the full B-domin and thus the methal ions between the A and B domain. Further a structure of the main part of the alpha-amylase from B. stearothermophilus has been published by Sued [?] and the structure of the alkaline alpha amylase SP722 was presended in WO 01/66712.

To build the best model of a given alpha-amylase, the structure of the closed homolog is chosed, i.e. a good model of B. licheniformis alpha amylase is best build on basis of the structure of BA2, so is a good model of B. amyloliquefacience alpha-amylase, while alkaline alpha-amylases like AA560, SP707, SP7-7 and KSM-AP1378 are best build on the structure of SP722 α-amylase.

Homology Building of AA560 from SP722 Tertiary Structure

The overall homology of the AA560 alpha-amylase (SEQ ID NO: 12) to SP722 (SEQ ID NO: 4) is about 87% as described above. Sequence alignment of AA560 and SP722 shows where to be no insertion or deletions, which can also be seen in FIG. 1.

The tertiary structure of the AA560 alpha-amylase was model build on the structure disclosed in Appendix 1 using the method "Modelbuiling" described in the "Materials & Methods"-section.

The structure of SP722 was displayed on a UNIX work staion running Insight and Homology software from BIO-SYM, MSI. The amino acid sequences were aligned and the Sp722 coordinated assigned to the AA560 amino acids. The coordinates of the first four amino acids in AA560, which are missing in the SP722 structure, were assigned by the "END REPAIR" function.

The AA560 model was refined by first relaxing the amino acid side changes, using the "RELAX" command and then running molecular dynamics to minimise the energy of the 3D model. Default parameters from Insight 95, MSI were chosen for both relaxation molecular dynamics.

Fermentation and Purification of α-Amylase Variants

Fermentation and purification may be performed by methods well known in the art.

Fermentation of Alpha-Amylases and Variants

Fermentation may be performed by methods well known in the art or as follows:

A B. subtilis strain harboring the relevant expression plasmid is streaked on a LB-agar plate with a relevant antibiotic, and grown overnight at 37° C.

The colonies are transferred to 100 ml BPX media supplemented with a relevant antibiotic (for instance 10 mg/l chloroamphinicol) in a 500 ml shaking flask.

Composition of BPX Medium:

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| $Na_2HPO_4$, 12 $H_2O$ | 9 g/l |
| Pluronic ™ | 0.1 g/l |

The culture is shaken at 37° C. at 270 rpm for 4 to 5 days.

Cells and cell debris are removed from the fermentation broth by centrifugation at 4500 rpm in 20-25 minutes. Afterwards the supernatant is filtered to obtain a completely clear solution. The filtrate is concentrated and washed on an UF-filter (10000 cut off membrane) and the buffer is changed to 20 mM Acetate pH 5.5. The UF-filtrate is applied on a S-sepharose F.F. and elution is carried out by step elution with 0.2 M NaCl in the same buffer. The eluate is dialysed against 10 mM Tris, pH 9.0 and applied on a Q-sepharose F.F. and eluted with a linear gradient from 0-0.3M NaCl over 6 column volumes. The fractions, which contain the activity (measured by the Phadebas assay) are pooled, pH was adjusted to pH 7.5 and remaining color was removed by a treatment with 0.5% W/vol. active coal in 5 minutes.

Stability Determination

The amylase stability is measured using the method as follows:

The enzyme is incubated under the relevant conditions. Samples are taken at various time points, e.g., after 0, 5, 10, 15 and 30 minutes and diluted 25 times (same dilution for all taken samples) in assay buffer (0.1M 50 mM Britton buffer pH 7.3) and the activity is measured using the Phadebas assay (Pharmacia) under standard conditions pH 7.3, 37° C.

The activity measured before incubation (0 minutes) is used as reference (100%). The decline in percent is calculated as a function of the incubation time. The table shows the residual activity after, e.g., 30 minutes of incubation.

Measurement of the Calcium- and pH-Dependent Stability

Normally industrial liquefaction processes runs using pH 6.0-6.2 as liquefaction pH and an addition of 40 ppm free calcium in order to improve the stability at 95° C.-105° C. Some of the herein proposed substitutions have been made in order to improve the stability at 1. lower pH than pH 6.2 and/or
2. at free calcium levels lower than 40 ppm free calcium.

Two different methods can be used to measure the alterations in stability obtained by the different substitutions in the alpha-amylase in question:

Method 1.

One assay which measures the stability at reduced pH, pH 5.0, in the presence of 5 ppm free calcium.

10 micro g of the variant are incubated under the following conditions: A 0.1 M acetate solution, pH adjusted to pH 5.0, containing 5 ppm calcium and 5% w/w common corn starch (free of calcium). Incubation is made in a water bath at 95° C. for 30 minutes.

Method 2.

One assay, which measure the stability in the absence of free calcium and where the pH is maintained at pH 6.0. This assay measures the decrease in calcium sensitivity: 10 micro g of the variant were incubated under the following conditions: A 0.1 M acetate solution, pH adjusted to pH 6.0, containing 5% w/w common corn starch (free of calcium). Incubation was made in a water bath at 95° C. for 30 minutes.

Assays for Alpha-Amylase Activity

1. Phadebas Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

2. Alternative Method

Alpha-amylase activity is determined by a method employing the PNP-G7 substrate. PNP-G7 which is a abbreviation for p-nitrophenyl-alpha,D-maltoheptaoside is a blocked oligosaccharide which can be cleaved by an endo-amylase. Following the cleavage, the alpha-Glucosidase included in the kit digest the substrate to liberate a free PNP molecule which has a yellow colour and thus can be measured by visible spectophometry at $\lambda$=405 nm. (400-420 nm.). Kits containing PNP-G7 substrate and alpha-Glucosidase is manufactured by Boehringer-Mannheim (cat. No. 1054635).

To prepare the substrate one bottle of substrate (BM 1442309) is added to 5 ml buffer (BM1442309). To prepare the $\alpha$-Glucosidase one bottle of alpha-Glucosidase (BM 1462309) is added to 45 ml buffer (BM1442309). The working solution is made by mixing 5 ml alpha-Glucosidase solution with 1 ml substrate.

The assay is performed by transforming 20 µl enzyme solution to a 96 well microtitre plate and incubating at 25° C. 200 µl working solution, 25° C. is added. The solution is mixed and pre-incubated 1 minute and absorption is measured every 15 sec. over 3 minutes at OD 405 nm.

The slope of the time dependent absorption-curve is directly proportional to the specific activity (activity per mg enzyme) of the alpha-amylase in question under the given set of conditions.

Specific Activity Determination

The specific activity is determined as activity/mg enzyme using one of the methods described above. The manufactures instructions are followed (see also below under "Assay for alpha-amylase activity).

Oxidation Stability Determination

Raw filtered culture broths with different vatiants of the invention are diluted to an amylase activity of 100 KNU/ml (defined above) in 50 mM of a Britton-Robinson buffer at pH 9.0 and incubated at 40° C. Subsequently $H_2O_2$ is added to a concentration of 200 mM, and the pH value is re-adjusted to 9.0. The activity is now measured after 15 seconds and after 5, 15, and 30 minutes by taking out samples and dilute them 5 times with ice-cold water and store them on ice. The remaining activity is thus measured using the Phadebas methos as described above where the absorbance of the resulting blue solution, measured spectrophotometrically at 620 nm, is a function of the alpha-amylase activity. The activities after 5, 15 and 30 minutes are calculated relatively to the activity after 15 sec., to determine the stability.

Washing Performance

Washing performance is evaluated by washing soiled test swatches for 15 and 30 minutes at 25° C. and 40° C., respectively; at a pH in the range from 9-10.5; water hardness in the range from 6 to 15° dH; Ca:Mg ratio of from 2:1 to 4:1, in different detergent solutions (see above as described above in the Materials section) dosed from 3 to 5 g/l dependent on the detergent with the alpha-amylase variant in question.

The recombinant alpha-amylase variant is added to the detergent solutions at concentrations of for instance 0.01-5 mg/l. The test swatches are soiled with orange rice starch (CS-28 swatches available from CFT, Center for Test Material, Holland).

After washing, the swatches are evaluated by measuring the remission at 460 nm using an Elrepho Remission Spectrophotometer. The results are expressed as $\Delta R$=remission of the swatch washed with the alpha-amylase minus the remission of a swatch washed at the same conditions without the alpha-amylase.

EXAMPLES

Example 1

Construction of Variants of AA560 SEQ ID NO: 12

The gene encoding the AA560 alpha-amylase shown in SEQ ID NO: 12 is located in a plasmid pTVB223. The amylase is expressed from the amyL promoter in this construct in *Bacillus subtilis*.

A variant of the invention with M202L mutation was constructed by the mega-primer method as described by Sarkar and Sommer, (1990), BioTechniques 8: 404-407.

The resulting plasmid encoding the AX379 amylase with M202L was named pCA202-AX379

The construction of the other variants of the invention was carried out in a similar manner.

Example 2

Determination of Activity in Wash

Amylase variants were constructed using conventional methods in the amylase AX379 or AX413, respectively which in the activity test is used as reference (first line in the table). The AX413 variant is derived from AX379 by introducing mutations as indicated in the tables below.

The activity was measured in detergent solution in a simulated European wash at 40° C. A suspension of one Phadebas tablet per 5 ml of 4 g/L detergent solution was made and adequated under stirring into Eppendorf tubes. After 5 minutes of pre-heating at 40° C. Amylase enzyme was add and the mixture incubated for 20 min under vigorous shaking. The reaction is stopped by adding 10% 1M NaOH and the tubes are spin for 3 min at 10000×g as minimum. Finally the absorbance at 650 nm is measured for the supernatant using a non-enzyme sample as blind.

TABLE 3

| Mutations | Improvement in activity |
| --- | --- |
| AX379 | 1 |
| K118Q | 1.1 |
| K37T | 1.1 |
| H421Y | 1.1 |
| V450T | 1.1 |
| K383R | 1.1 |
| N445Q | 1.1 |
| Y178F | 1.2 |
| V318L | 1.2 |
| W482Y | 1.2 |
| N283D + Q361E | 1.2 |
| M105F + M208F | 1.2 |
| M202L + M323T + M430I | 1.3 |
| K446R + N484Q | 1.4 |
| R444Y | 1.5 |
| N106D | 1.8 |
| Y203L | 2.0 |
| G133E + Q361E | 2.9 |
| M323E | 4.1 |
| V214T | 6.8 |
| M202L + M323T + M309L | 13 |
| M202L | 16 |
| M202L + M323T | 23 |
| M202L + M323T + M9L + M382Y + K383R | 25 |
| M202L + M323T + M9L + M382Y | 26 |
| M202L + M323T + M9L (AX413) | 27 |

TABLE 4

| Mutations | Improvement in activity |
| --- | --- |
| AX413 | 1 |
| T461P | 1.1 |
| Y298H | 1.1 |
| G133E + R444E | 1.1 |
| Y298F | 1.1 |
| M202T | 1.2 |
| M202I | 1.6 |
| M202V | 1.6 |
| Y295F | 3.4 |

Example 3

Determination of Stability During Dishwash

Amylase variants were constructed using conventional methods in the amylase AX379 or AX413, respectively which in the activity test is used as reference (first line in the table). The AX413 variant is derived from AX379 by introducing mutations as indicated in the tables above.

The amylase stability was measured by incubating around 0.1 mg/ml amylase in 4 g/l detergent for automatic dishwash at 40° C. for 18 hours. The incubation was stopped by adding 9 volumes of cold (<5° C.) water and stored on ice. With one hour the activity was measured using the Phadebas Amylase kit and the activity in detergent samples compared to samples incubated for the same period in detergent but on ice.

TABLE 5

| Mutations | Improvement in residual activity |
| --- | --- |
| AX413 | 1 |
| V214T + M323E + M382Y + K383R + N471E | 1.1 |
| Y178F + G258D + T419N + N437H | 1.1 |
| G149N + N150Q + M382Y + K383R | 1.1 |
| Y160F + V214T + M382Y | 1.2 |
| N128Y + G149A + V214T + D231N + M382Y + F441L | 1.2 |
| R82H + N128Y + G149A + V214T + M382Y | 1.2 |
| N150H + V214T | 1.2 |
| V214T + E345N | 1.2 |
| V214T + G305D + M382Y + R444E | 1.2 |
| V214T + M382Y + A447Y | 1.2 |
| M202I + V214T + M382Y + K383R + R444Y | 1.2 |
| V214T + G378K | 1.3 |
| V214T + A256K | 1.3 |
| R26S + D30N + N33D + V214T + M382Y | 1.5 |

Example 4

Amylase variants of seq. ID no. 12 were constructed as described in example 1 and fermented in shakeflasks using a rich media. From the supernatant the amylase variant protein was purified using standard purification methods to above 90% purity. The protein concentration was calculated from A280 absorbance and a theoretic extension coefficient of 2.9 ml/mg/cm.

The G7-pNP activity assay was used as described under "Methods" to measure the activity of the amylase samples and thus the specific activity (SA), i.e. the G7-pNP activity per mg of amylase protein was calculated and compared to a homologous reference amylase.

| | Rel. SA |
| --- | --- |
| M202L (Ref.A) | 1.00 |
| Ref.A + M9L + M323T | 1.18 |
| Ref.A + M9L + M323T + M382Y + K383R | 1.20 |
| Ref.A + M9L + S303Q + M323T + M382Y + K383R | 1.31 |
| Ref.A + M9L + V214T + M323T + M382Y | 1.37 |
| Ref.A + M9L + M323T + A339S + M382Y + K383R + N471E | 1.55 |
| Ref.A + M9L + V214T + M323T + A339S + N471E | 1.73 |

| | Rel. SA |
| --- | --- |
| M202L + V214T (Ref.B) | 1.00 |
| Ref.B + G149H | 1.41 |
| Ref.B + E345R | 1.18 |

-continued

| | Rel. SA |
|---|---|
| Ref.B + G149A + M382Y | 1.24 |
| Ref.B + G149A + N299Y + T356I + M382Y | 1.27 |
| Ref.B + M382Y | 1.43 |
| Ref.B + G149A + K269S + N270Y + Y295F + A339S + E345R + N471E | 1.78 |
| Ref.B + A339S + N471E | 1.80 |

| | Rel. SA |
|---|---|
| M9L + M202I + M323T (Ref.C) | 1.00 |
| Ref.C + V214T + Y295F + A339S + M382Y + K383R + N471E | 2.60 |

| | Rel. SA |
|---|---|
| M9L + M202I + V214T + Y295F + M323T + M382Y (Ref.D) | 1.00 |
| Ref.D + G149A + A339S + E345R | 1.25 |
| Ref.D + G149A + V214I + A339S | 1.25 |
| Ref.D + N83S + G149A + A339S + E345R | 1.25 |
| Ref.D + G133K + G149A + A339S + E345R | 1.33 |
| Ref.D + I206F + A339S | 1.42 |
| Ref.D + G149A + A339S | 1.50 |
| Ref.D + G149A + V214V + K269S + N270Y + E345R + A339S | 4.08 |
| Ref.D + G149A + V214V + K269S + N270Y + A339S | 5.83 |

| | IF |
|---|---|
| AX379 | 1.00 |
| M9L + G149A + M202I + V214T + Y295F + M323T + A339S + E345R + M382Y | 1.06 |
| G149A + G182T + G186A + M202I + V214T + Y295F + N299Y + M323T + A339S | 1.12 |
| M9L + G149A + M202I + V214I + Y295F + M323T + A339S + M382Y | 1.13 |
| M9L + N106D + M202L + M323T | 1.14 |
| M9L + M202L + M323T + M382Y + K383R | 1.14 |
| M9L + M202L + V214T + Y295F + M323T + M382Y | 1.14 |
| M9L + G133K + G149A + M202I + V214T + Y295F + M323T + A339S + E345R + M382Y | 1.14 |
| M9L + M202I + V214T + M323T + A339S + M382Y + K383R + N471E | 1.16 |
| M9L + M202L + V214T + M323T + M382Y | 1.17 |
| M9L + G149A + M202L + V214T + M323T + M382Y | 1.17 |
| M9L + M202L + S303Q + M323T + M382Y + K383R | 1.17 |
| M9L + G149A + G182T + M202L + T257I + Y295F + S303Y + M323T + A339S + E345R | 1.17 |
| M9L + G149A + M202L + V214T + N299Y + M323T + T356I + M382Y | 1.18 |
| M9L + G149H + M202L + V214T + M323T | 1.20 |
| M9L + M202L + V214T + M323T + E345R | 1.25 |
| M9L + G149A + G182T + M202L + T257I + Y295F + N299Y + M323T + A339S + E345R | 1.25 |
| M9L + G149A + M202L + V214I + Y295F + M323T + A339S | 1.26 |
| M9L + G149A + M202L + V214I + Y295F + M323T + A339S + E345R | 1.30 |
| M9L + M202L + V214T + Y295F + M323T + A339S | 1.31 |
| M9L + G149A + G182T + G186A + M202L + T257I + Y295F + N299Y + M323T + A339S + E345R | 1.35 |
| M9L + M202L + M323T + A339S + M382Y + K383R + N471E | 1.38 |

Example 5

Wash tests were conducted using 9 g/l (Henkel) HDD traditional detergent with bleach and 0.2 mg amylase protein per liter in a down scaled washing machine, applying a general European heat-up profile to 40° C. over 20 minutes. The water hardness is adjusted with Ca, Mg and $NaHCO_3$ to 16° dH.

The washing performance is evaluated on cotton swatches with colored rice starch, (CS-28 from CFT), by measuring the whiteness of the swatch after wash with amylase present relative to the whiteness of a swatch washed without amylase. The whiteness is measured using a remission spectrophotometer (Macbeth Color-Eye), after the swathes have dried on lines over night.

Example 6

Wash tests were conducted using 6 g/l Persil Megaperls (Henkel) detergent and 0.2 mg amylase protein per liter in a down scaled washing machine, applying a general European heat-up profile to 40° C. over 20 minutes. The water hardness is adjusted with Ca, Mg and $NaHCO_3$ to 16° dH.

The washing performance is evaluated on cotton swatches with colored rice starch, (CS-28 from CFT), by measuring the whiteness of the swatch after wash with amylase present relative to the whiteness of a swatch washed without amylase. The whiteness is measured using a remission spectrophotometer (Macbeth Color-Eye), after the swathes have dried on lines over night.

The invention claimed is:

1. An isolated variant of a parent Termamyl-like alpha-amylase, comprising an alteration at one or more positions selected from the group of:
R26S, D30N, N33D, R82H, K37T, N106D, N128Y, G133E,A, G149A,N, N150H,Q, Y160F, Y178F, Y203L, V214I,T, D231N, G256K, T257I, G258D, N270F,Y,D, L272I,V,A, N283D, Y295F,N,D,Q,E, N296K,Q,E, Y304F,R,K, G305D, G315N,S,T, V318L, A339S,T, Q361E, G378K, T419N, H421Y, F441L, K446R, A447Y, V450T, T461P, and W482Y, wherein
the variant has alpha-amylase activity, and wherein
each position corresponds to a position of the amino acid sequence of the parent alpha-amylase having the amino acid sequence of the parent Termamyl-like alpha-amylase having the amino acid sequence of AA560 shown in SEQ ID NO: 12, wherein the variant has an amino acid sequence which has a degree of identity of at least 90% to SEQ ID NO: 12.

2. The variant of claim 1, wherein the variant has an additional mutation in one or more methionine residues.

3. The variant of claim 2, wherein the methionine residues are:
M9, M10, M116, M202, M208, M261, M309, M323, M382, M410, M430, and M440.

4. The variant of claim 2, wherein the mutations are:
M9L,I, M10L, M105L,I,F, M116N,D,L,I,F,W,R,K, M202I,L,V,T, M208F,Y,L,I, M261 L,I, M309L,I, M323L,I,S,T,A,Q,E,N,D, M382L,I,Y,F,K, M410L,I,V, M430L,I, and M440L,I,F,Y.

5. The variant of claim 1, wherein the variant further comprises one or more of the following mutations:
M9L+M202I,
M9L+M202I+M323T,
M9L+M202I+323T+M382Y,
M9L+M202I+Y295F+A339S,
M9L+M202I+Y295F,
M9L+M202I+A339S,
M9L+M202I+Y295F+A339S,
M9L+M202I+Y295F+A339S+E345R,
M9L+G149A+M202I+Y295F+A339S+E345R,
M9L+M202L,
M9L+M202L+M323T,
M9L+M202L+M232T+M382Y,
M9L+M202L+Y295F+A339S,
M9L+M202L+Y295F,
M9L+M202L+A339S,
M9L+M202L+Y295F+A339S,
M9L+M202L+Y295F+A339S, E345R,
M9L+G149A+M202L+Y295F+A339S+E345R,
M9L+M202T,
M9L+M202T+M323T,
M9L+M202T+M323T+M382Y,
M9 L+M202T+Y295F+A339S,
M9L+M202T+Y295F,
M9L+M202T+A339S,
M9 L+M202T+Y295F+A339S,
M9L+M202T+Y295F+A339S+E345R,
M9L+G149A+M202T+Y295F+A339S+E345R,
M9L+G149A+M202I+V214T+Y295F+N299Y+M323T+A339S+E345R,
M9L+G149A+M202L+V214I+Y295F+M323T+A339S+E345R+M382Y,
M9L+G149A+G182T+M202I+V214I+Y295F+N299Y+M323T+A339S,
M9L+G149A+G182T+M202L+T257I+Y295F+N299Y+M323T+A339S+E345R,
M9L+G149A+M202L+V214T+Y295F+N299Y+M323T+A339S+E345R,
M9L+G149A+M202I+V214I+Y295F+M323T+A339S+E345R+M382Y,
M9L+G149A+G182T+M202L+V214I+Y295F+N299Y+M323T+A339S, M9L+G149A+G182T+M202I+T257I+Y295F+N299Y+ M323T+A339S+E345R,
M9L+G149A+M202I+V214T+Y295F+N299Y+ M323T+A339S+E345R+N471E,
M9L+G149A+M202L+V214I+Y295F+M323T+ A339S+E345R+M382Y+N471E,
M9L+G149A+G182T+M202I+V214I+Y295F+N299Y+ M323T+A339S+N471E,
M9L+G149A+G182T+M202L+T257I+Y295F+N299Y+ M323T+A339S+E345R+N471E,
M202L+M105F+M208F,
G133E+M202L+Q361E,
G133E+M202L+R444E,
M202L+Y295F,
M202 L+A339S,
M202 L+M323T,
M202L+M323T+M309L,
M202L+M323T+M430I,
M202L+V214T+R444Y,
M202L+N283D+Q361E,
M202L+M382Y+K383R,
M202L+K446R,
M202I+Y295F,
M202I+A339S,
M202I+M105F+M208F,
G133E+M202I+Q361E,
G133E+M202I+R444E,
M202I+M202I+M323T,
M202I+M202I+M323T+M309L,
M202I+M323T+M430I,
M202I+V214T+R444Y,
M202I+N283D+Q361E,
M202I+M382Y+K383R,
M202I+K446R,
M202V+M105F+M208F,
G133E+M202V+Q361E,
G133E+M202V+R444E,
M202V+M323T,
M202V+M323T+M309L,
M202V+M323T+M430I,
M202V+M323T+M9L,
M202V+V214T+R444Y,
M202V+N283D+Q361E,
M202V+M382Y+K383R,
M202V+K446R,
M202T+M105F+M208F,
G133E+M202T+Q361E,
G133E+M202T+R444E,
M202T+Y295F,
M202T+A339S,
M202T+M323T,
M202T+M323T+M309L,
M202T+M323T+M430I,
M202T+M323T+M9L,
M202T+V214T+R444Y,
M202T+N283D+Q361E,
M202T+A339S,
M202T+Y295F
M202T+N299F,Y,
M202T+M382Y+K383R,
M202T+K446R.

6. The variant of claim 1, wherein the variant further comprises the mutation D183*+G184*.

7. The variant of claim 1, wherein the variant further comprises a mutation in R118.

8. The variant of claim 1, wherein the variant further comprises a mutation in N195.

9. The variant of claim 1, wherein the variant further comprises a mutation in R320.

10. The variant of claim 1, wherein the variant further comprises a mutation in R458.

11. The variant of claim 1, wherein the variant further comprises the mutation D183*+G184*+R118K+N195F+ R320K+R458K in combination with one or more of the following mutations:
K37T,
H421Y,
V450T,
K383R,
N445Q,
Y178F,
V318L,
W482Y,
N283D+Q361E,
M105F+M208F,
M202L+M323T+M430I,
K446R,
R444Y,
N106D,
Y203L,
G133E+Q361E,
M323E,
V214T,
M202L+M323T+M309L,
M202L,
M202L+M323T,
M202L+M323T+M9L+M382Y+K383R,
M202L+M323T+M9L+M382Y,
M202L+M323T+M9L.

12. The variant of claim 1, wherein the variant further comprises the mutation D183*+G184*+R118K+N195F+ R320K+R458K+M202L+M323T+M9L.

13. The variant of claim 1, wherein the variant further comprises one or more of the following mutations:
T461P,
Y298H,
G133E+R444E,
Y298F,
M202T,
M202I,
M202V,
V214T+M323E+M382Y+K383R+N471E
Y178F+G258D+T419N+N437H
G149N+N150Q+M382Y+K383R
Y160F+V214T+M382Y
N128Y+G149A+V214T+D231N+M382Y+F441L
R82H+N128Y+G149A+V214T+M382Y
N150H+V214T
V214T+E345N
V214T+G305D+M382Y+R444E
V214T+M382Y+A447Y
M202I+V214T+M382Y+K383R+R444Y
V214T+G378K
V214T+A256K
R26S+D30N+N33D+V214T+M382Y.

14. The variant of claim 1, wherein the parent Termamyl-like alpha-amylase is depicted in SEQ ID NO: 12.

15. The variant of claim 1, wherein the parent Termamyl-like alpha-amylase is encoded by a nucleic acid sequence, which hybridizes under high stringency conditions, with the nucleic acid sequence of SEQ ID NO: 11.

16. A detergent additive comprising an alpha-amylase variant according to claim 1.

17. The isolated variant of a parent Termamyl-like alpha-amylase of claim 1, wherein the variant has an amino acid sequence which has a degree of identity of at least 95% to SEQ ID NO: 12.

18. The isolated variant of a parent Termamyl-like alpha-amylase of claim 1, wherein the variant has an amino acid sequence which has a degree of identity of at least 96% to SEQ ID NO: 12.

19. The isolated variant of a parent Termamyl-like alpha-amylase of claim 1, wherein the variant has an amino acid sequence which has a degree of identity of at least 97% to SEQ ID NO: 12.

20. The isolated variant of a parent Termamyl-like alpha-amylase of claim 1, wherein the variant has an amino acid sequence which has a degree of identity of at least 98% to SEQ ID NO: 12.

21. The isolated variant of a parent Termamyl-like alpha-amylase of claim 1, wherein the variant has an amino acid sequence which has a degree of identity of at least 99% to SEQ ID NO: 12.

* * * * *